(12) United States Patent
Rhad et al.

(10) Patent No.: US 9,414,816 B2
(45) Date of Patent: Aug. 16, 2016

(54) INTRODUCER FOR BIOPSY DEVICE

(75) Inventors: Edward A. Rhad, Fairfield, OH (US);
John A. Hibner, Mason, OH (US);
Andrew P. Nock, Centerville, OH (US);
Kyle P. Moore, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 574 days.

(21) Appl. No.: 13/166,918

(22) Filed: Jun. 23, 2011

(65) Prior Publication Data
US 2012/0330186 A1 Dec. 27, 2012

(51) Int. Cl.
*A61B 10/02* (2006.01)

(52) U.S. Cl.
CPC ..... *A61B 10/0275* (2013.01); *A61B 2010/0208* (2013.01)

(58) Field of Classification Search
USPC .................................. 600/562–568
See application file for complete search history.

(56) References Cited

U.S. PATENT DOCUMENTS

| | | | | |
|---|---|---|---|---|
| 5,104,378 A | * | 4/1992 | Haber et al. | 604/110 |
| 5,209,739 A | * | 5/1993 | Talalay | 604/195 |
| 5,263,937 A | * | 11/1993 | Shipp | 604/166.01 |
| 5,364,365 A | * | 11/1994 | Wortrich | 604/158 |
| 5,385,151 A | | 1/1995 | Scarfone et al. | |
| 5,526,822 A | | 6/1996 | Burbank et al. | |
| 5,649,547 A | * | 7/1997 | Ritchart et al. | 600/566 |
| 5,709,671 A | * | 1/1998 | Stephens et al. | 604/264 |
| 5,752,970 A | * | 5/1998 | Yoon | 606/185 |
| 5,797,927 A | * | 8/1998 | Yoon | 606/144 |
| 5,800,389 A | | 9/1998 | Burney et al. | |
| 5,824,002 A | * | 10/1998 | Gentelia et al. | 604/164.11 |
| 6,030,364 A | * | 2/2000 | Durgin et al. | 604/164.01 |
| 6,086,544 A | | 7/2000 | Hibner et al. | |
| 6,228,055 B1 | | 5/2001 | Foerster et al. | |
| 6,234,177 B1 | | 5/2001 | Barsch | |
| 6,277,083 B1 | * | 8/2001 | Eggers et al. | 600/564 |

(Continued)

FOREIGN PATENT DOCUMENTS

| | | |
|---|---|---|
| CN | 1084729 A | 4/1994 |
| CN | 1706348 A | 12/2005 |

(Continued)

OTHER PUBLICATIONS

International Search Report and Written Opinion dated Dec. 14, 2012 for Application No. PCT/US2012/041188.

(Continued)

*Primary Examiner* — Sean Dougherty
(74) *Attorney, Agent, or Firm* — Frost Brown Todd LLC

(57) ABSTRACT

A biopsy system comprises an introducer, a biopsy device having a needle, and a marker applier. The introducer may include a closed distal tip, a lateral aperture, a proximally facing interior wall, and a ramp that guides the closed distal end of a marker applier up and into abutment with the wall as the applier is fed into the introducer. The needle of the biopsy device includes a blunt distal end and features providing clearance for the ramp as the blunt distal end is brought into abutment with the wall when the needle is fed into the introducer. The introducer may alternatively include an open distal end having resiliently biased leaves that bear against an inserted biopsy device needle. In some other versions, a fin projects laterally from the closed distal end of a marker applier, spacing the distal end away from a sidewall region of the introducer cannula.

12 Claims, 18 Drawing Sheets

(56) References Cited

U.S. PATENT DOCUMENTS

| | | | |
|---|---|---|---|
| 6,371,904 B1 | 4/2002 | Sirimanne et al. | |
| 6,436,119 B1* | 8/2002 | Erb et al. | 606/198 |
| 6,626,849 B2 | 9/2003 | Huitema et al. | |
| 6,993,375 B2 | 1/2006 | Burbank et al. | |
| 6,996,433 B2 | 2/2006 | Burbank et al. | |
| 7,044,957 B2 | 5/2006 | Foerster et al. | |
| 7,047,063 B2 | 5/2006 | Burbank et al. | |
| 7,189,249 B2* | 3/2007 | Hart et al. | 606/185 |
| 7,229,417 B2 | 6/2007 | Foerster et al. | |
| 7,442,171 B2 | 10/2008 | Stephens et al. | |
| 7,465,279 B2 | 12/2008 | Beckman et al. | |
| 7,507,210 B2 | 3/2009 | Hibner et al. | |
| 7,604,648 B2* | 10/2009 | Kerr | 606/198 |
| 7,670,350 B2 | 3/2010 | Selis | |
| 7,722,550 B2* | 5/2010 | McClellan | 600/567 |
| 7,854,706 B2 | 12/2010 | Hibner | |
| 8,079,964 B2 | 12/2011 | Reichel et al. | |
| 8,105,345 B2* | 1/2012 | Golden et al. | 606/153 |
| 8,251,068 B2* | 8/2012 | Schnell | 128/207.29 |
| 8,343,035 B2* | 1/2013 | To | 600/109 |
| 8,394,063 B2 | 3/2013 | Riek et al. | |
| 8,394,114 B2* | 3/2013 | Schaller et al. | 606/153 |
| 8,480,676 B2* | 7/2013 | Lyon | 606/86 R |
| 8,529,465 B2* | 9/2013 | Speeg et al. | 600/562 |
| 2005/0203419 A1 | 9/2005 | Ramanujam et al. | |
| 2006/0030785 A1* | 2/2006 | Field et al. | 600/567 |
| 2006/0074345 A1 | 4/2006 | Hibner | |
| 2006/0200042 A1* | 9/2006 | Weikel et al. | 600/566 |
| 2007/0213633 A1* | 9/2007 | McClellan | 600/564 |
| 2007/0249939 A1* | 10/2007 | Gerbi et al. | 600/462 |
| 2008/0015429 A1* | 1/2008 | Tsonton et al. | 600/414 |
| 2008/0214955 A1 | 9/2008 | Speeg et al. | |
| 2008/0281223 A1* | 11/2008 | Goldenberg | 600/567 |
| 2008/0281226 A1* | 11/2008 | Peters | 600/567 |
| 2009/0131790 A1* | 5/2009 | Munrow et al. | 600/439 |
| 2009/0209853 A1 | 8/2009 | Parihar et al. | |
| 2009/0209854 A1 | 8/2009 | Parihar et al. | |
| 2009/0247900 A1* | 10/2009 | Zimmer | 600/564 |
| 2009/0270725 A1 | 10/2009 | Leimbach et al. | |
| 2009/0270892 A1* | 10/2009 | Arcenio et al. | 606/170 |
| 2010/0049084 A1 | 2/2010 | Nock et al. | |
| 2010/0114031 A1* | 5/2010 | Jarial et al. | 604/164.11 |
| 2010/0152610 A1 | 6/2010 | Parihar et al. | |
| 2010/0160819 A1 | 6/2010 | Parihar et al. | |
| 2010/0160822 A1* | 6/2010 | Parihar et al. | 600/567 |
| 2010/0160824 A1 | 6/2010 | Parihar et al. | |
| 2010/0317997 A1 | 12/2010 | Hibner et al. | |
| 2011/0071391 A1 | 3/2011 | Speeg | |
| 2011/0071423 A1 | 3/2011 | Speeg et al. | |
| 2011/0071424 A1 | 3/2011 | Nock et al. | |
| 2011/0071431 A1 | 3/2011 | Speeg et al. | |
| 2011/0092850 A1* | 4/2011 | Kulkarni et al. | 600/562 |
| 2011/0092916 A1* | 4/2011 | Tezel et al. | 604/241 |
| 2011/0282242 A1* | 11/2011 | Cronin et al. | 600/567 |
| 2012/0016260 A1* | 1/2012 | To | 600/562 |
| 2012/0123296 A1* | 5/2012 | Hashimshony et al. | 600/567 |

FOREIGN PATENT DOCUMENTS

| | | |
|---|---|---|
| CN | 101053508 A | 10/2007 |
| CN | 101653382 A | 2/2010 |
| EP | 0773002 A1 | 5/1997 |
| EP | 1582168 | 10/2005 |
| EP | 1598015 A1 | 11/2005 |
| EP | 1759638 A1 | 3/2007 |
| EP | 2216069 B1 | 1/2014 |
| JP | 2005-288175 A | 10/2005 |
| WO | WO 99/17665 | 4/1999 |
| WO | WO 2011/022122 | 2/2011 |

OTHER PUBLICATIONS

U.S. Appl. No. 12/709,695, filed Feb. 22, 2010, Hibner et al.
U.S. Appl. No. 12/875,200, filed Sep. 3, 2010, Speeg et al.
U.S. Appl. No. 12/953,715, filed Nov. 24, 2010, Rhad et al.
U.S. Appl. No. 61/381,466, filed Sep. 10, 2010, Hibner.
Chinese Office Action dated Dec. 2, 2014 for Application No. CN 201280029965.2.
Chinese Office Action dated Jun. 16, 2015 for Application No. CN 201280029965.2.
Chinese Office Action dated Oct. 21, 2015 for Application No. CN 201280029965.2.
Chinese Office Action, Notification of Grant, dated Jan. 21, 2016 for Application No. CN 201280029965.2.
Extended European Search Report dated Mar. 3, 2015 for Application No. EP 12803348.7.
European Search Report and Written Opinion dated Jan. 22, 2016 for Application No. EP 15187481.5.
Japanese Office Action dated Nov. 17, 2015 for Application No. JP 2014-516996.

* cited by examiner

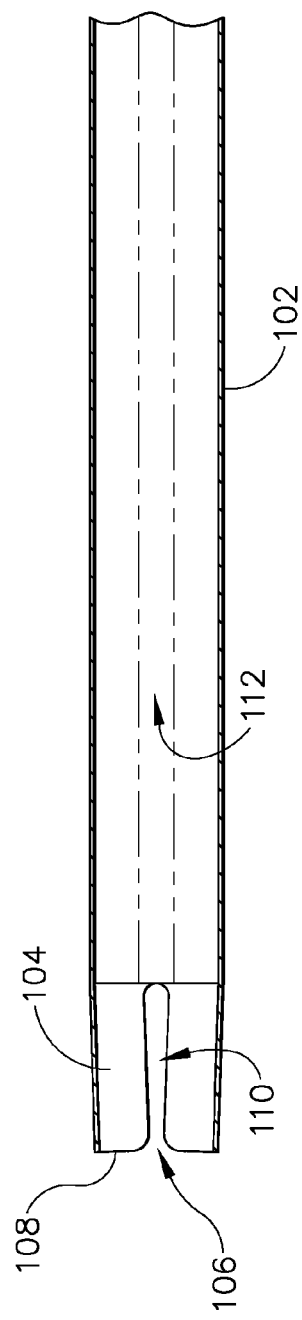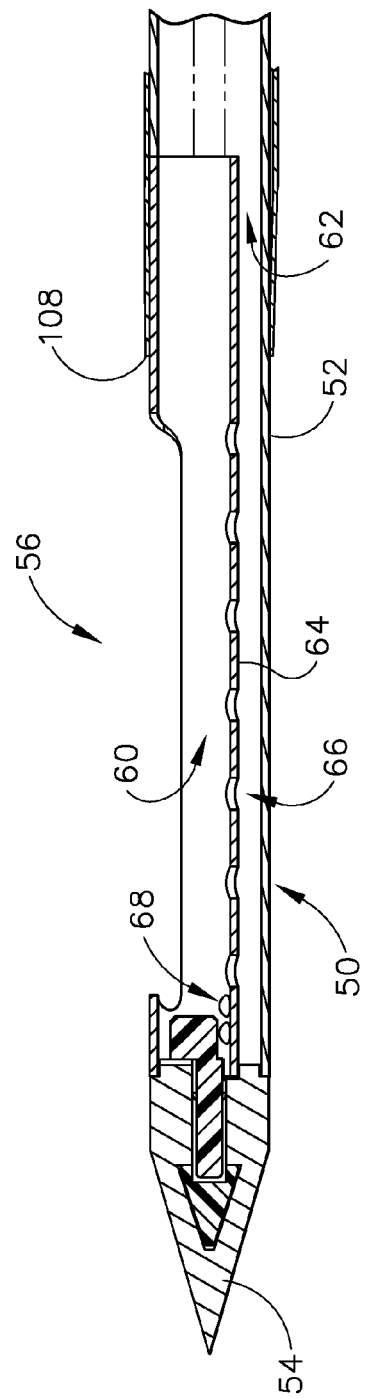

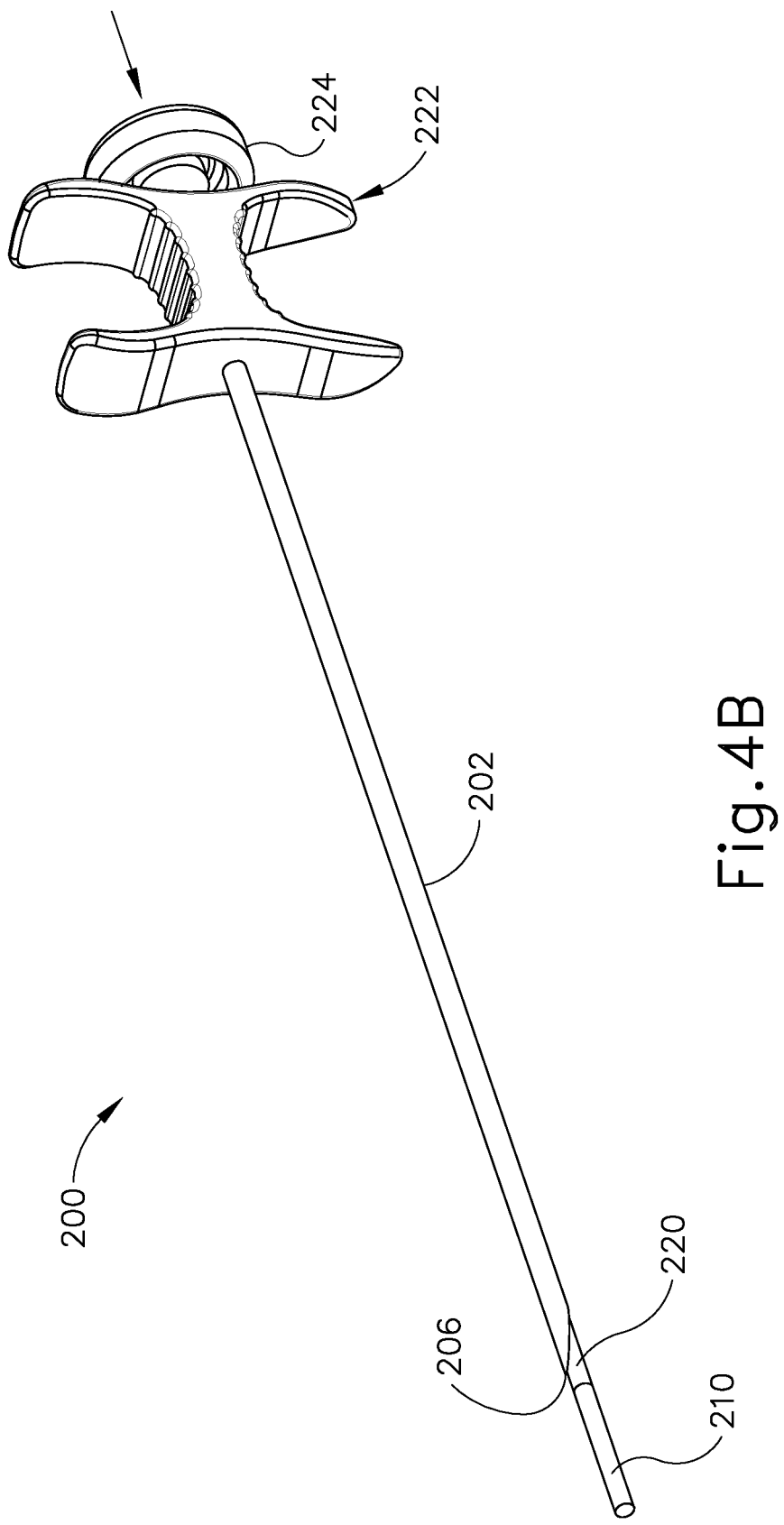

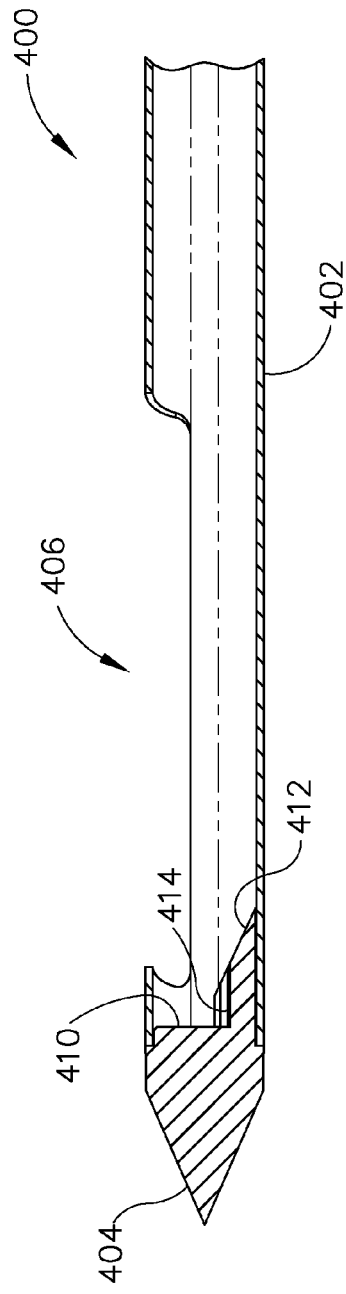
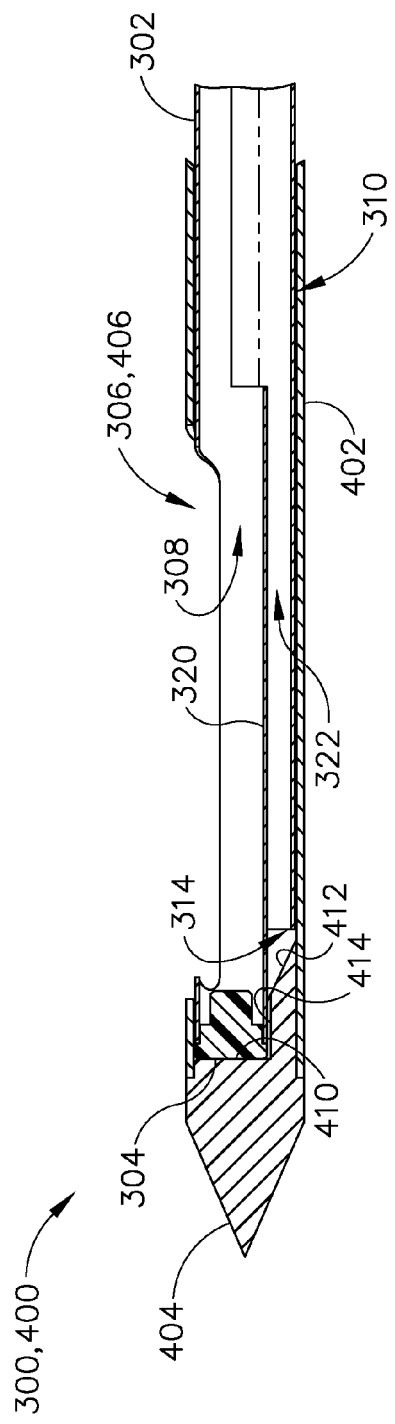
Fig.8A
Fig.8B

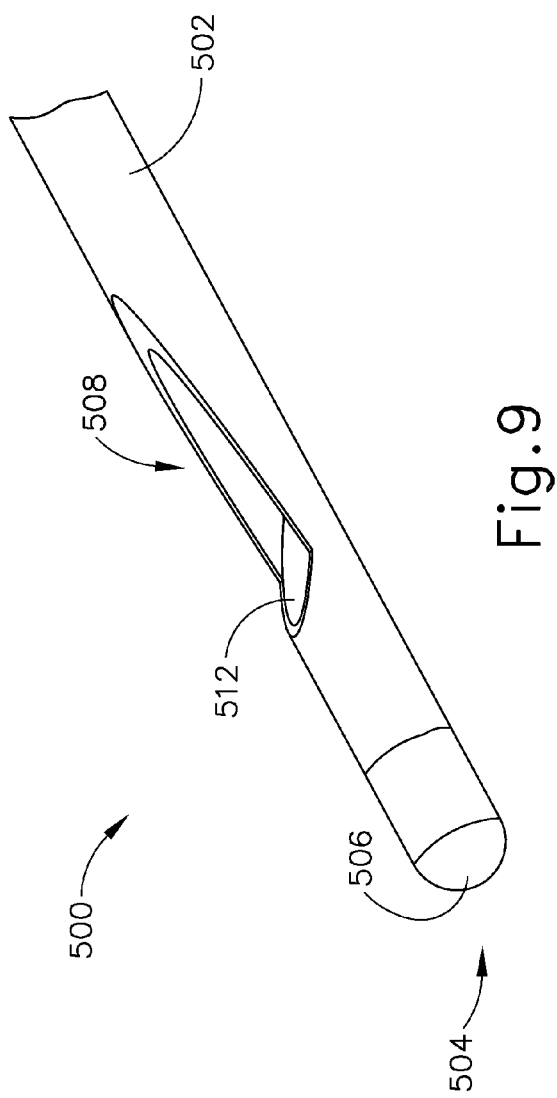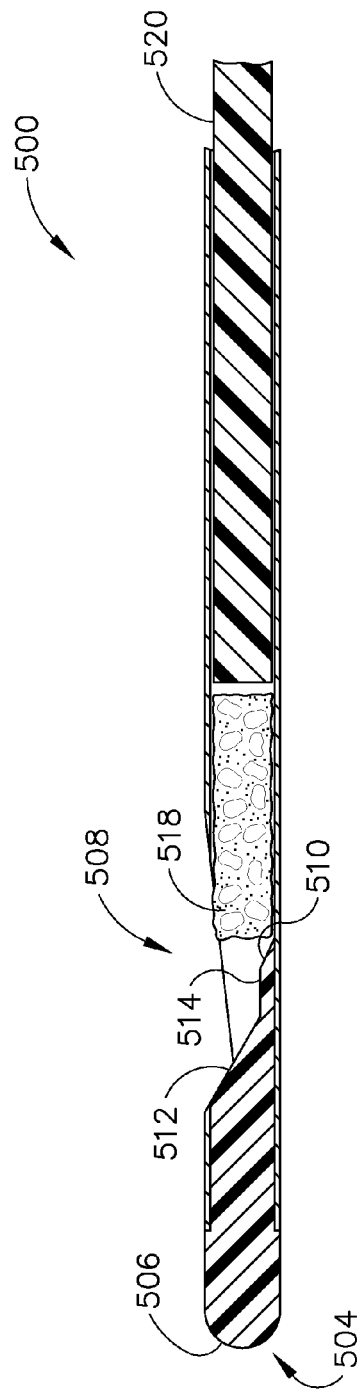
Fig.9
Fig.10

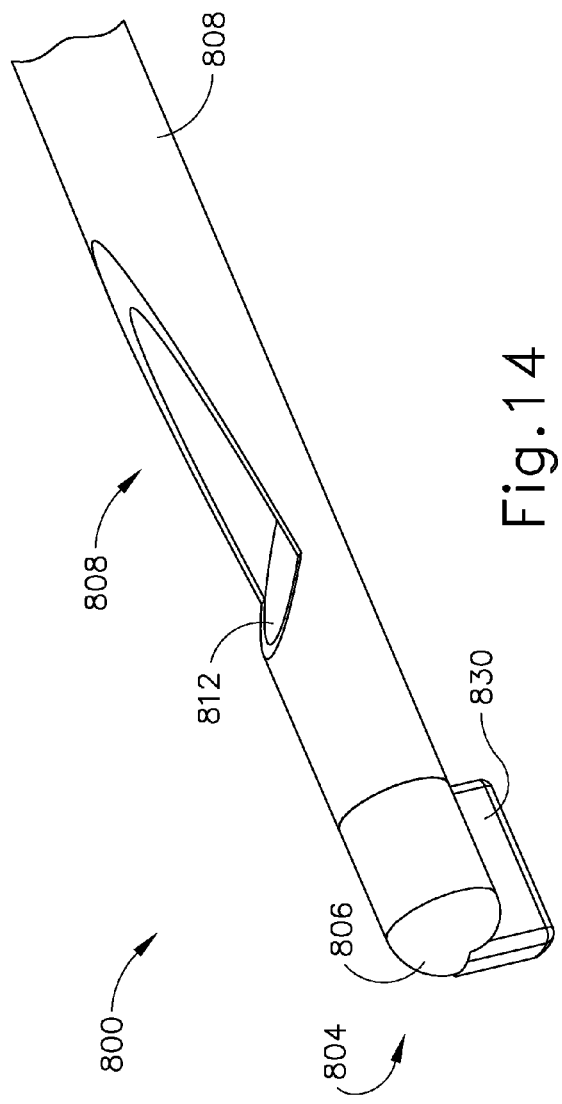
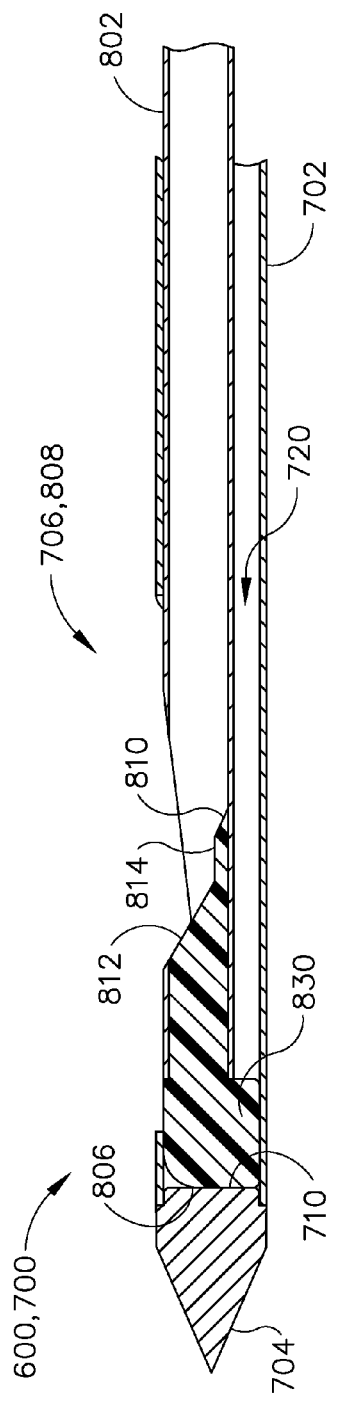

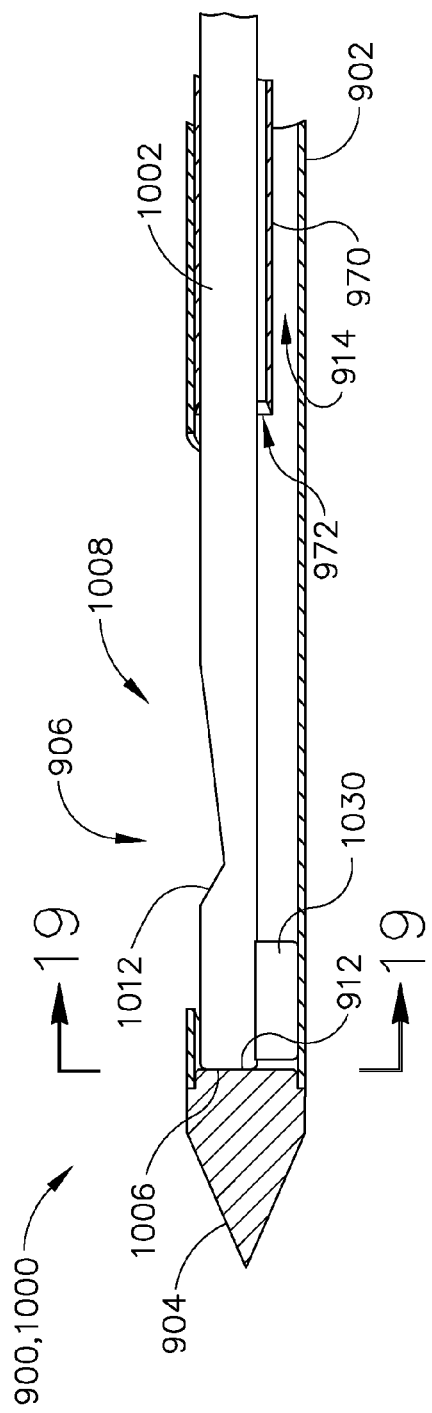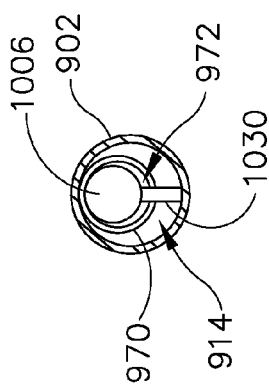

INTRODUCER FOR BIOPSY DEVICE

BACKGROUND

Biopsy samples have been obtained in a variety of ways in various medical procedures using a variety of devices. Biopsy devices may be used under simple visual guidance, palpatory guidance, stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pat. No. 7,507,210, entitled "Biopsy Cannula Adjustable Depth Stop," issued Mar. 24, 2009; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. Pub. No. 2010/0152610, entitled "Hand Actuated Tetherless Biopsy Device with Pistol Grip," published Jun. 17, 2010; U.S. Pub. No. 2010/0160819, entitled "Biopsy Device with Central Thumbwheel," published Jun. 24, 2010; U.S. Pub. No. 2010/0317997, entitled "Tetherless Biopsy Device with Reusable Portion," published Dec. 16, 2010; and U.S. Non-Provisional patent application Ser. No. 12/953,715, entitled "Handheld Biopsy Device with Needle Firing," filed Nov. 24, 2010. The disclosure of each of the above-cited U.S. Patents, U.S. Patent Application Publications, and U.S. Non-Provisional Patent Applications is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK™, MICROMARK®, and CORMARK™ brand devices from Devicor Medical Products, Inc. of Cincinnati, Ohio. Further exemplary devices and methods for marking a biopsy site are disclosed in U.S. Pub. No. 2009/0209854, entitled "Biopsy Method," published Aug. 20, 2009; U.S. Pub. No. 2009/0270725, entitled "Devices Useful in Imaging," published Oct. 29, 2009; U.S. Pub. No. 2010/0049084, entitled "Biopsy Marker Delivery Device," published Feb. 25, 2010; U.S. Pub. No. 2011/0071423, entitled "Flexible Biopsy Marker Delivery Device," published Mar. 24, 2011; U.S. Pub. No. 2011/0071424, entitled "Biopsy Marker Delivery Device," published Mar. 24, 2011; U.S. Pub. No. 2011/0071391, entitled "Biopsy Marker Delivery Device with Positioning Component," published Mar. 24, 2011; U.S. Pat. No. 6,228,055, entitled "Devices for Marking and Defining Particular Locations in Body Tissue," issued May 8, 2001; U.S. Pat. No. 6,371,904, entitled "Subcutaneous Cavity Marking Device and Method," issued Apr. 16, 2002; U.S. Pat. No. 6,993,375, entitled "Tissue Site Markers for In Vivo Imaging," issued Jan. 31, 2006; U.S. Pat. No. 6,996,433, entitled "Imageable Biopsy Site Marker," issued Feb. 7, 2006; U.S. Pat. No. 7,044,957, entitled "Devices for Defining and Marking Tissue," issued May 16, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; and U.S. Pat. No. 7,465,279, entitled "Marker Device and Method of Deploying a Cavity Marker Using a Surgical Biopsy Device," issued Dec. 16, 2008. The disclosure of each of the above-cited U.S. Patents and U.S. Patent Application Publications is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 2A depicts a partial, side cross-sectional view of the introducer cannula of FIG. 1A;

FIG. 2B depicts a partial, side cross-sectional view of the needle of the biopsy device and the introducer cannula of FIG. 1A, with the needle of the biopsy device inserted in the introducer cannula;

FIG. 4B depicts a perspective view of the marker applier of FIG. 4A, with the plunger of the marker applier in a distal position to deploy a marker;

FIG. 8A depicts a partial, side cross-sectional view of the introducer cannula of FIG. 7;

FIG. 8B depicts a partial, side cross-sectional view of the needle of FIG. 6 inserted in the introducer cannula of FIG. 7;

FIG. 9 depicts a perspective view of an exemplary alternative distal end configuration for the marker applier of FIG. 4A;

FIG. 10 depicts a partial, side cross-sectional view of the marker applier of FIG. 9;

FIG. 14 depicts a perspective view of another exemplary alternative distal end configuration for the marker applier of FIG. 4A;

FIG. 15 depicts a partial, side cross-sectional view of the marker applier of FIG. 14 inserted in the introducer cannula of FIG. 13A;

FIG. 18 depicts a partial, side cross-sectional view of the marker applier, cutter, and needle of FIG. 16, with the distal end of the marker applier positioned distal to the distal end of the cutter;

FIG. 19 depicts a cross-sectional view of the marker applier, cutter, and needle of FIG. 16, taken along line 19-19 of FIG. 18;

Figure 1A:
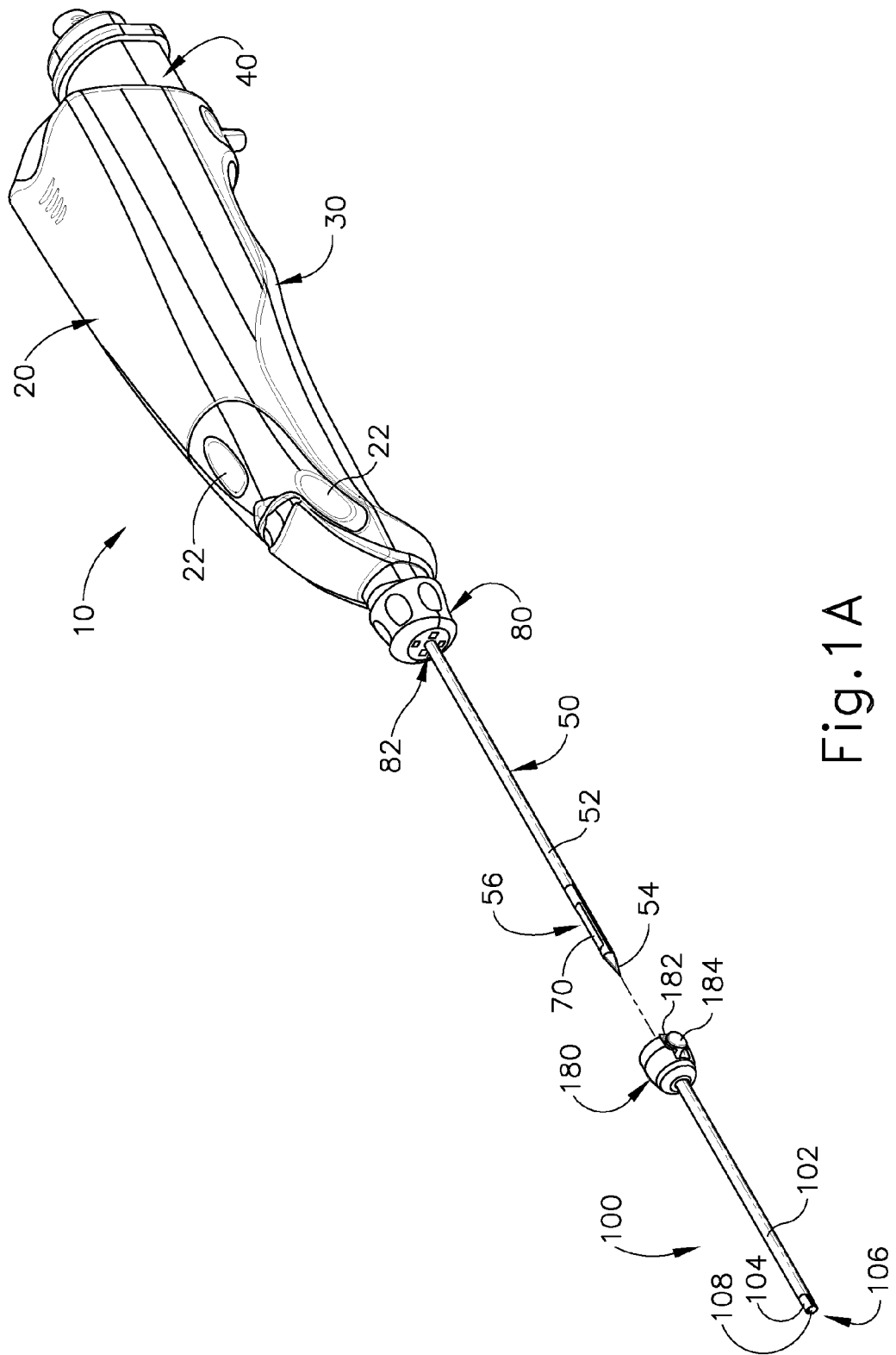
FIG. 1A depicts a perspective view of an exemplary biopsy device and an exemplary introducer cannula, with the introducer cannula separated from the biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary Biopsy Device

FIGS. 1A-2B show an exemplary biopsy device (10). Biopsy device (10) of this example comprises a probe (30) and a holster (20). A needle (50) extends distally from probe (30), and is inserted into a patient's tissue to obtain tissue samples as will be described in greater detail below. These tissue samples are deposited in a tissue sample holder (40) at the proximal end of probe (30), as will also be described in greater detail below. Probe (30) is removably coupled with holster (20) in the present example. It should be understood that the use of the term "holster" herein should not be read as requiring any portion of probe (30) to be inserted into any portion of holster (20). A variety of types of structures, components, features, etc. (e.g., bayonet mounts, latches, clamps, clips, snap fittings, etc.) may be used to provide removable coupling of probe (30) and holster (20). Furthermore, in some biopsy devices (10), probe (30) and holster (20) may be of unitary or integral construction, such that the two components cannot be separated. By way of example only, in versions where probe (30) and holster (20) are provided as separable components, probe (30) may be provided as a disposable component, while holster (20) may be provided as a reusable component. Still other suitable structural and functional relationships between probe (30) and holster (20) will be apparent to those of ordinary skill in the art in view of the teachings herein.

Needle (50) of the present example includes a cannula (52), a piercing tip (54), a lateral aperture (56) located proximal to tip (54), and a hub member (80). Tissue piercing tip (54) is configured to pierce and penetrate tissue, without requiring a high amount of force, and without requiring an opening to be pre-formed in the tissue prior to insertion of tip (54). Alternatively, tip (54) may be blunt (e.g., rounded, flat, etc.) if desired, including but not limited to having any of the alternative configurations described below. Tip (54) may also be configured to provide greater echogenicity than other portions of needle (50), providing enhanced visibility of tip (54) under ultrasound imaging. By way of example only, tip (54) may be configured in accordance with any of the teachings in U.S. Non-Provisional patent application Ser. No. 12/875,200, entitled "Echogenic Needle for Biopsy Device," filed Sep. 3, 2010, the disclosure of which is incorporated by reference herein. Other suitable configurations that may be used for tip (54) will be apparent to those of ordinary skill in the art in view of the teachings herein.

Lateral aperture (56) is sized to receive prolapsed tissue during operation of device (10). A hollow tubular cutter (70) having a sharp distal edge (not shown) is located within a first lumen (60) of needle (50). Cutter (70) is operable to rotate and translate relative to needle (50) and past lateral aperture (56) to sever a tissue sample from tissue protruding through lateral aperture (56). For instance, cutter (70) may be moved from an extended position (FIG. 1) to a retracted position (FIG. 2B), thereby "opening" lateral aperture (56) to allow tissue to protrude therethrough; then from the retracted position back to the extended position to sever the protruding tissue. Mechanical components in holster (20) and probe (30) may cooperate to provide such actuation of cutter (70), as described in any reference cited herein or otherwise. As another merely illustrative example, cutter (70) may be actuated pneumatically in addition to or in lieu of being actuated by mechanical components. Other suitable alternative versions, features, components, configurations, and functionalities for providing cutter actuation will be apparent to those of ordinary skill in the art in view of the teachings herein.

While lateral aperture (56) is shown oriented in an upward position in FIG. 1, it should be understood that needle (50) may be manually rotated to orient lateral aperture (56) at any desired angular position about the longitudinal axis of needle (50). Such rotation of needle (50) is facilitated in the present example by hub member (80). Hub member (80) may be constructed and operable in accordance with the teachings of U.S. Non-Provisional patent application Ser. No. 12/953,715 and/or in any other suitable fashion. Various other suitable ways in which manual rotation of needle (50) may be provided will be apparent to those of ordinary skill in the art in view of the teachings herein. It should also be understood that rotation of needle (50) may be automated in various ways, including but not limited to the various forms of automatic or mechanized needle rotation described in various references that are cited herein.

As best seen in FIG. 2B, needle (50) also includes a longitudinal wall (64) extending proximally from the proximal portion of tip (54). While wall (64) does not extend along the full length of needle (50) in this example, it should be understood that wall (64) may extend the full length of needle (50) if desired. Wall (64) defines a second lumen (62) that is lateral to and parallel to cutter (70). Wall (64) includes a plurality of openings (66) that provide fluid communication between second lumen (62) and first lumen (60), as well as fluid communication between second lumen (62) and the lumen (not shown) of cutter (70). For instance, second lumen (62) may selectively provide atmospheric air to vent the lumen of cutter (70) during operation of biopsy device (10). Openings (66) are arranged such that at least one opening (68) is located at a longitudinal position that is distal to the distal edge of lateral aperture (56). Thus, the lumen of cutter (70) and second lumen (62) may remain in fluid communication even when cutter (70) is advanced to a position where the distal cutting edge of cutter (70) is located at a longitudinal position that is distal to the longitudinal position of the distal edge of lateral aperture (56). Of course, as with any other component described herein, any other suitable configurations may be used.

Probe (30) may also include a valve assembly in fluid communication with at least part of needle (50), selectively changing a pneumatic state of at least part of needle (50) based on any suitable conditions such as the longitudinal position of cutter (70). For instance, such a valve assembly may selectively change the pneumatic state of second lumen (62). Such a valve assembly may be constructed in accordance with the teachings of U.S. Pub. No. 2010/0317997; in accordance with the teachings of U.S. Non-Provisional patent application Ser. No. 12/953,715; and/or otherwise. In addition or in the alternative, valving may be provided by a vacuum source and/or a vacuum canister, such as is taught in U.S. Pub. No. 2008/0214955. Other suitable alternative versions, features, components, configurations, and functionalities of needle (50) will be apparent to those of ordinary skill in the art in view of the teachings herein.

Tissue sample holder (40) of the present example is configured to receive tissue samples that are severed by cutter (70) and communicated proximally through the hollow interior of cutter (70). Tissue sample holder (40) may include one or more removable trays (not shown) that permit a user to remove severed tissue samples from tissue sample holder (40) without having to remove tissue sample holder (40) from probe (30). In some such versions, tissue sample holder (40) is constructed in accordance with the teachings of U.S. Provisional Patent App. No. 61/381,466, entitled "Biopsy Device Tissue Sample Holder with Removable Basket," filed Sep. 10, 2010, the disclosure of which is incorporated by reference herein. In addition or in the alternative, tissue sample holder (130) may include a rotatable manifold (not shown) that is in fluid communication with a vacuum source and cutter (70); and that is rotatable to successively index separate tissue receiving chambers to cutter (70). By way of example only, tissue sample holder (40) may be constructed and operable in accordance with the teachings of U.S. Pub. No. 2008/0214955, the disclosure of which is incorporated by reference herein. As another merely illustrative example, tissue sample holder (40) may be constructed and operable in accordance with the teachings of U.S. Pub. No. 2010/0160824, entitled "Biopsy Device with Discrete Tissue Chambers," published Jun. 24, 2010, the disclosure of which is incorporated by reference herein. Still other suitable ways in which tissue sample holder (40) may be constructed and operable will be apparent to those of ordinary skill in the art in view of the teachings herein.

Biopsy device (10) may also include a vacuum source (not shown), such as a vacuum pump. By way of example only, a vacuum source may be incorporated into probe (30), incorporated into holster (20), and/or be a separate component altogether. In versions where a vacuum source is separate from probe (30) and holster (20), the vacuum source may be coupled with probe (30) and/or holster (20) via one or more conduits such as flexible tubing. It should also be understood that a vacuum source may be in fluid communication with tissue sample holder (40) and needle (50). Thus, the vacuum source may be activated to draw tissue into lateral aperture (56) of needle (50). Tissue sample holder (40) is also in fluid communication with cutter (70) in the present example. A vacuum source may thus also be activated to draw severed tissue samples through the hollow interior of cutter (70) and into tissue sample holder (40). In some versions, a vacuum source is provided in accordance with the teachings of U.S. Pub. No. 2008/0214955. In addition or in the alternative, a vacuum source may be provided in accordance with the teachings of U.S. Non-Provisional patent application Ser. No. 12/953,715. As yet another merely illustrative example, a vacuum source may be provided in accordance with the teachings of U.S. Non-Provisional patent application Ser. No. 12/709,695, entitled "Biopsy Device with Auxiliary Vacuum Source," filed Feb. 22, 2010, the disclosure of which is incorporated by reference herein. Still other suitable ways in which a vacuum source may be provided will be apparent to those of ordinary skill in the art in view of the teachings herein. It should also be understood that a vacuum source may simply be omitted, if desired.

Biopsy device (10) of the present example is sized and configured such that biopsy device (10) may be operated by a single hand of a user. In particular, a user may grasp biopsy device (10), insert needle (50) into a patient's breast, and collect one or a plurality of tissue samples from within the patient's breast, all with just using a single hand. Alternatively, a user may grasp biopsy device (10) with more than one hand and/or with any desired assistance. It should also be understood that biopsy device (10) may be configured to mount to a table or fixture, and be used under stereotactic guidance. Of course, biopsy device (10) may instead be used under ultrasound guidance, MRI guidance, PEM guidance, BSGI guidance, or otherwise. In some settings, the user may capture a plurality of tissue samples with just a single insertion of needle (50) into the patient's breast. Such tissue samples may be pneumatically deposited in tissue sample holder (40), and later retrieved from tissue sample holder (40) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Other suitable components, features, configurations, and operabilities for biopsy device (10) will be apparent to those of ordinary skill in the art in view of the teachings herein.

II. Exemplary Introducer Cannula with Open Distal End

In some settings, needle (50) is inserted directly into a patient's tissue, such that the outer surface of the entire inserted length of cannula (52) comes in direct contact with the patient's tissue. In some other versions, an introducer cannula is used. By way of example only, an introducer cannula having an open distal tip may first be inserted into the patient's tissue. In some instances, an obturator having a sharp distal tip (that protrudes from the open distal end of the introducer cannula) may be disposed in the introducer cannula when the two are inserted into the patient's tissue. If an obturator is used during insertion into the patient's tissue, the obturator may be removed after the introducer cannula has reached a desired depth in the tissue. Needle (50) and/or other instruments may then be fed into the introducer cannula to reach the tissue at the distal end of the cannula.

Figure 1B:
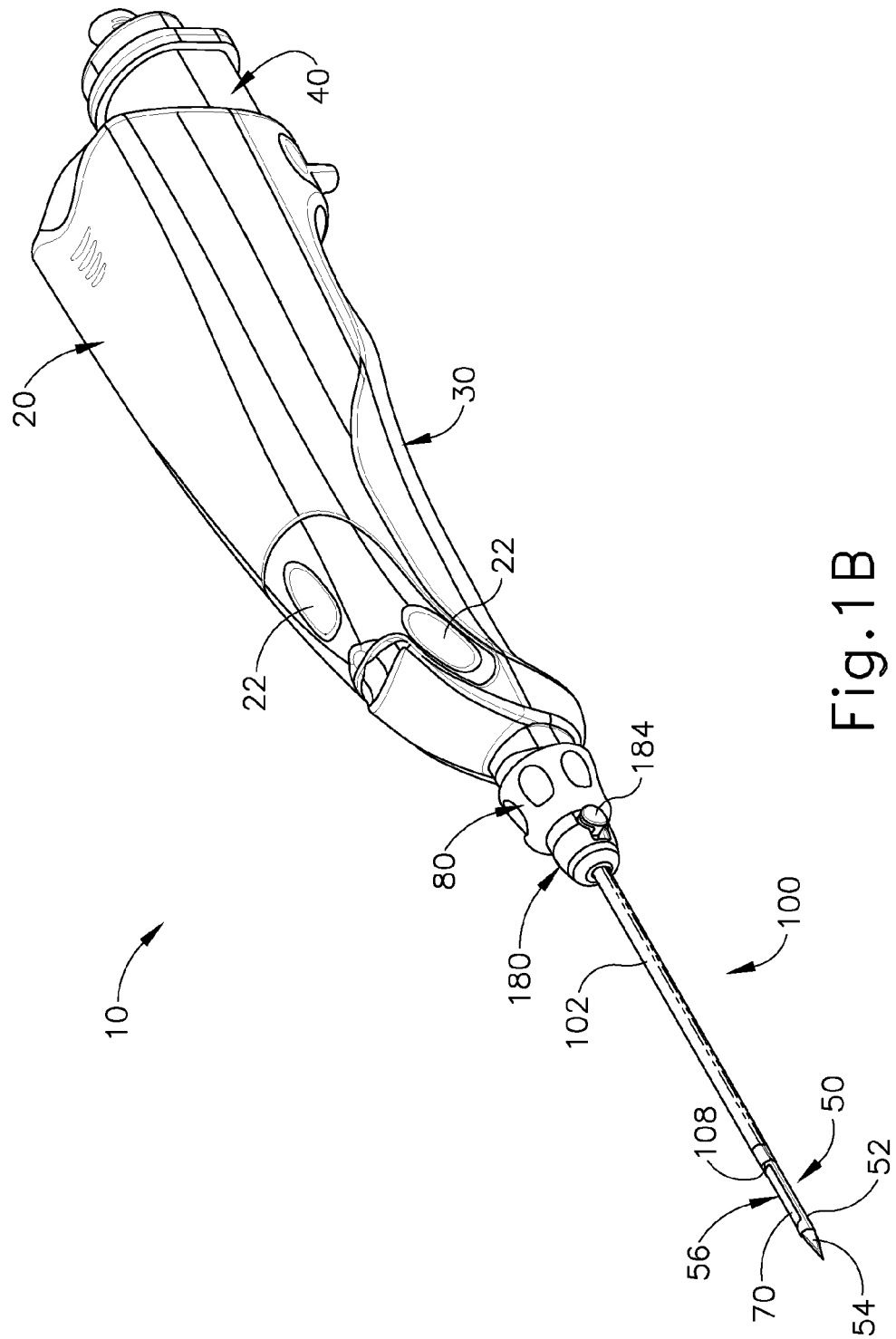
FIG. 1B depicts a perspective view of the biopsy device and introducer cannula of FIG. 1A, with the needle of the biopsy device inserted in the introducer cannula.

In some settings, such as those where the needle of a biopsy device has a sharp tip, the introducer may be coupled with the needle before the two are inserted together into the patient's tissue. A merely illustrative example of this is shown in FIGS. 1A-2B. In particular, FIG. 1A shows biopsy device (10) and an exemplary introducer (100) before needle (50) of biopsy device (10) is inserted in introducer (100). FIG. 1B shows needle (50) inserted in introducer (100). As seen in FIGS. 1A-1B, introducer (100) of this example comprises a cannula (102), a pair of distal leaves (104) at an open distal end (106), and a latching feature (180). Latching feature (180) is operable to selectively secure introducer (100) to biopsy device (10) as will be described in greater detail below. As seen in FIG. 2A, cannula (102) defines an internal lumen (112) that is in fluid communication with open distal end (106). As also seen in FIG. 2A, leaves (104) are resiliently biased to deflect slightly inwardly, yet a gap (110) is defined between leaves (104) to facilitate independent movement of leaves (104) toward or away from each other.

As best seen in FIGS. 1B and 2B, when cannula (52) of needle (50) is fully inserted into lumen (112) of cannula (102), a distal portion of needle (50) protrudes distally from cannula (102). In particular, lateral lumen (56) is fully exposed, being positioned distal to distal edges (108) of leaves (104). As can also be seen by comparing FIG. 2A (relaxed leaves (104)) to FIG. 2B (stressed leaves (104)), the outer diameter of cannula (52) is greater than the inner diameter defined between relaxed leaves (104), such that cannula (52) deflects leaves (104) outwardly when cannula (52) is inserted in cannula (102). In particular, leaves (104) are deflected such that they are substantially aligned with proximal portions of the sidewall of cannula (102). Leaves (104) thus resiliently bear against cannula (52) of needle (50). In some versions, distal edges (108) of leaves (104) are chamfered, providing a substantially smooth transition from the outer diameter of cannula (52) to the outer diameter of cannula (102).

In an exemplary use, introducer (100) is coupled with needle (50) as shown in FIGS. 1B and 2B. With cutter (70) at a distal position to effectively close lateral aperture (56), introducer (100) and needle (50) are then inserted together into a patient's tissue. Tip (54) pierces and penetrates the patient's tissue during this insertion. Cutter (70) is then reciprocated to acquire one or more tissue samples, which are deposited into tissue sample holder (40) (e.g., using vacuum assistance, etc.). Once the desired number of tissue samples have been acquired, needle (50) is decoupled from introducer (100), and cannula (52) is withdrawn from cannula (102), leaving cannula (102) disposed in the patient's tissue. A marker applier may then be inserted into lumen (112) of cannula (102) to deposit one or more markers at the biopsy site. In addition or in the alternative, one or more medicaments, brachytherapy pellets, and/or other substances may be applied at the biopsy site through lumen (112) of cannula (102). In addition or in the alternative, a variety of other kinds of instruments may be inserted through lumen (112) of cannula (102) to reach the biopsy site. Introducer (100) may then be pulled from the patient's tissue. Still other suitable ways in which introducer (100) may be used will be apparent to those of ordinary skill in the art in view of the teachings herein.

Figure 3A:
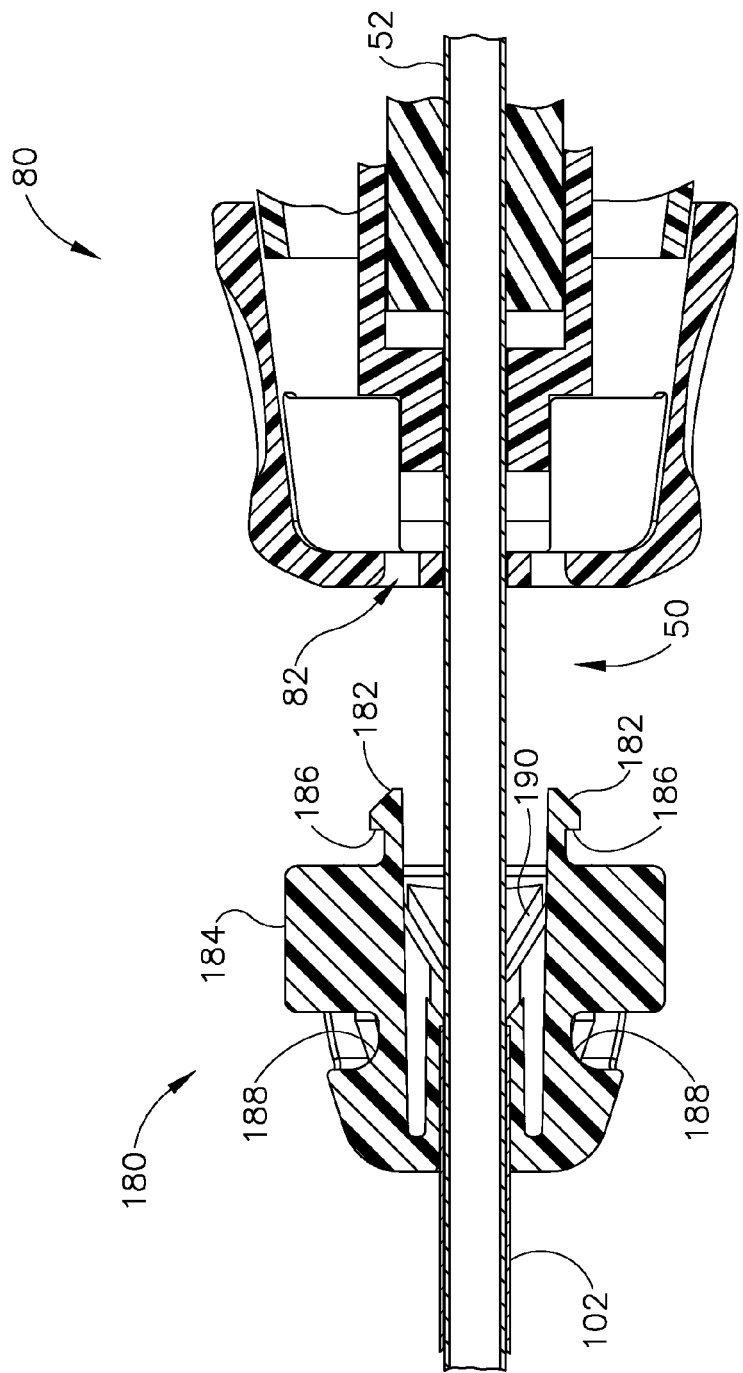
FIG. 3A depicts a partial, top cross-sectional view of latching features of the biopsy device and introducer cannula of FIG. 1A, with the latching features uncoupled from each other.
Figure 3B:
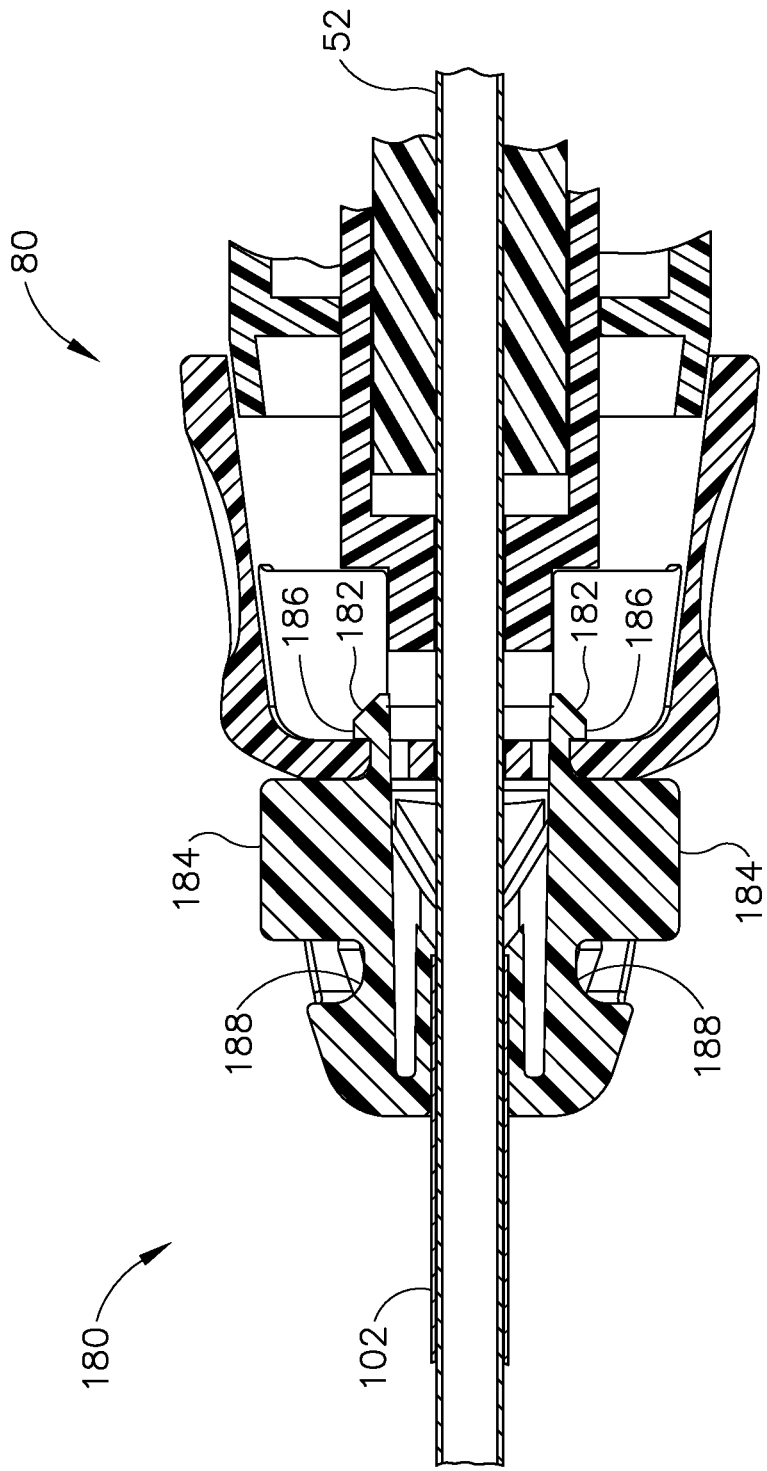
FIG. 3B depicts a partial, top cross-sectional view of the latching features of FIG. 3A, with the latching features coupled with each other.

Introducer (100) of the present example is operable to selectively couple with biopsy device (10) through a latching feature (180). As best seen in FIGS. 3A-3B, latching feature (180) of this example comprises a pair of latches (182) and associated buttons (184). Latches (182) are received in complementary slots (82) of hub member (80). Latches (182) include outward projections (186) that retain latches (182) in hub member (80). Latches (182) and buttons (184) are positioned on resilient arms (188), which resiliently bias latches (182) to the positions shown in FIGS. 3A-3B yet allow latches (182) to be deflected inwardly to accommodate insertion in slots (82) of hub member (80). Arms (188) also allow buttons (184) to be pressed inwardly toward each other to decouple latches (182) from slots (82). As can also be seen in FIGS. 3A-3B, the interior of latching feature (180) includes ramps (190) that help guide the distal end of cannula (52) into lumen (112) of introducer (100). While not shown, it should be understood that introducer may include one or more internal valves or seals, such as to reduce or prevent leakage of bodily fluids from introducer (100). It should also be understood that an introducer (100) may selectively couple with a biopsy device (10) in various other ways. Other suitable variations for latching feature (180) will be apparent to those of ordinary skill in the art in view of the teachings herein. Furthermore, introducer (100) need not necessarily be securable to biopsy device (10), such that latching feature (180) and variations thereof may simply be omitted if desired.

Figure 4A:
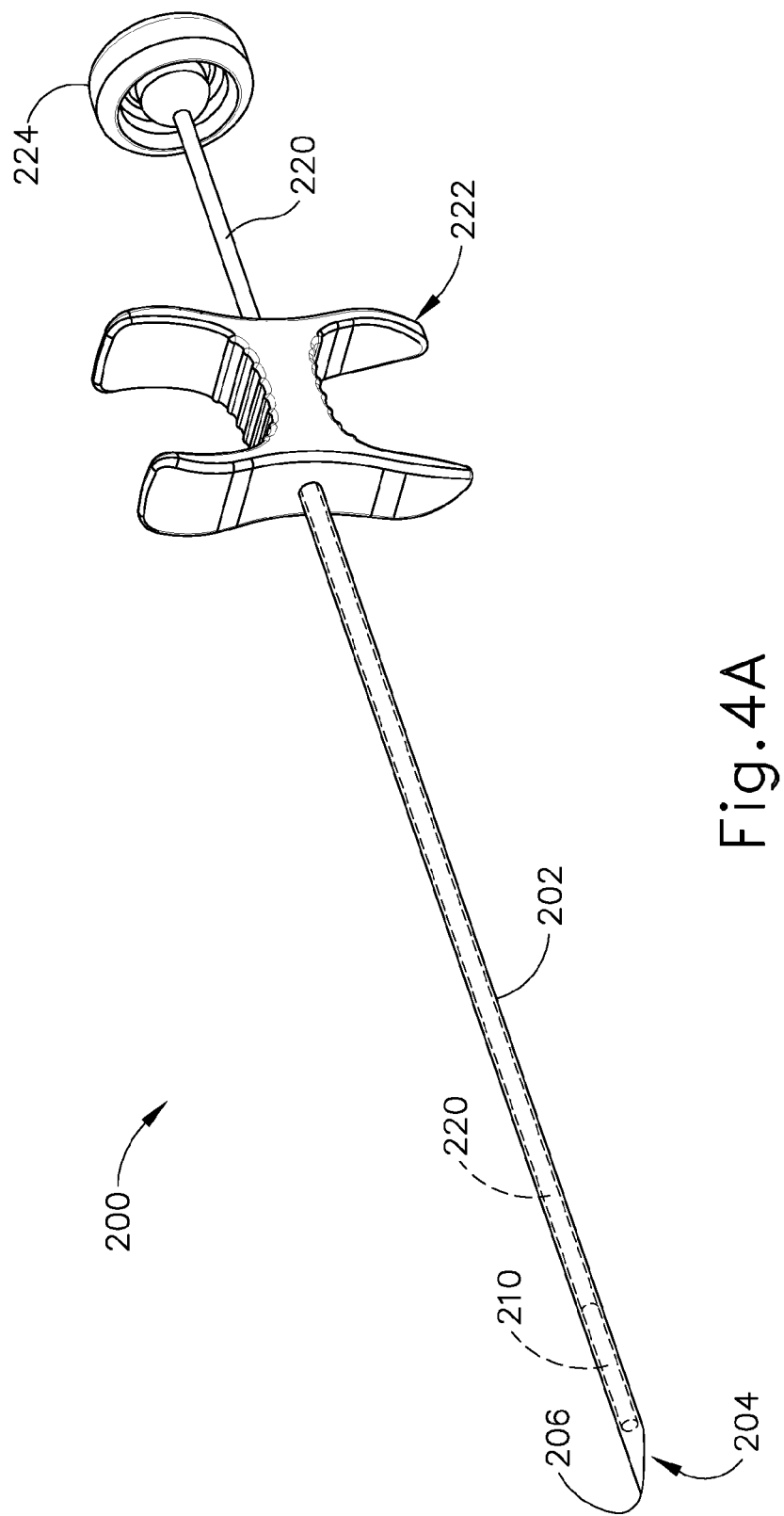
FIG. 4A depicts a perspective view of an exemplary biopsy site marker applier, with the plunger of the marker applier in a proximal position.

As noted above, if needle (50) is withdrawn from introducer (100) with introducer (100) remaining within the patient's tissue, introducer (100) may be used to guide a biopsy site marker applier instrument to the biopsy site for deployment of one or more biopsy site markers. For instance, FIGS. 4A-4B show an exemplary marker applier (200) that may be used with introducer (100). Marker applier (200) of this example comprises a cannula (202) having an open distal end (204) with a sharp tip (206). A biopsy site marker (210) is slidably disposed within cannula (202). A push rod (220) is also slidably disposed in cannula (202), and is operable to push marker (210) out through open distal end (204), as shown in FIG. 4B. A finger grip (222) and plunger (224) may be manipulated by a single hand of a user to hold marker applier (200) and to advance push rod (220) distally for deployment of marker (210). By way of example only, marker applier (200) comprises a CORMARK™ device from Devicor Medical Products, Inc. of Cincinnati, Ohio in some versions.

Figure 5:
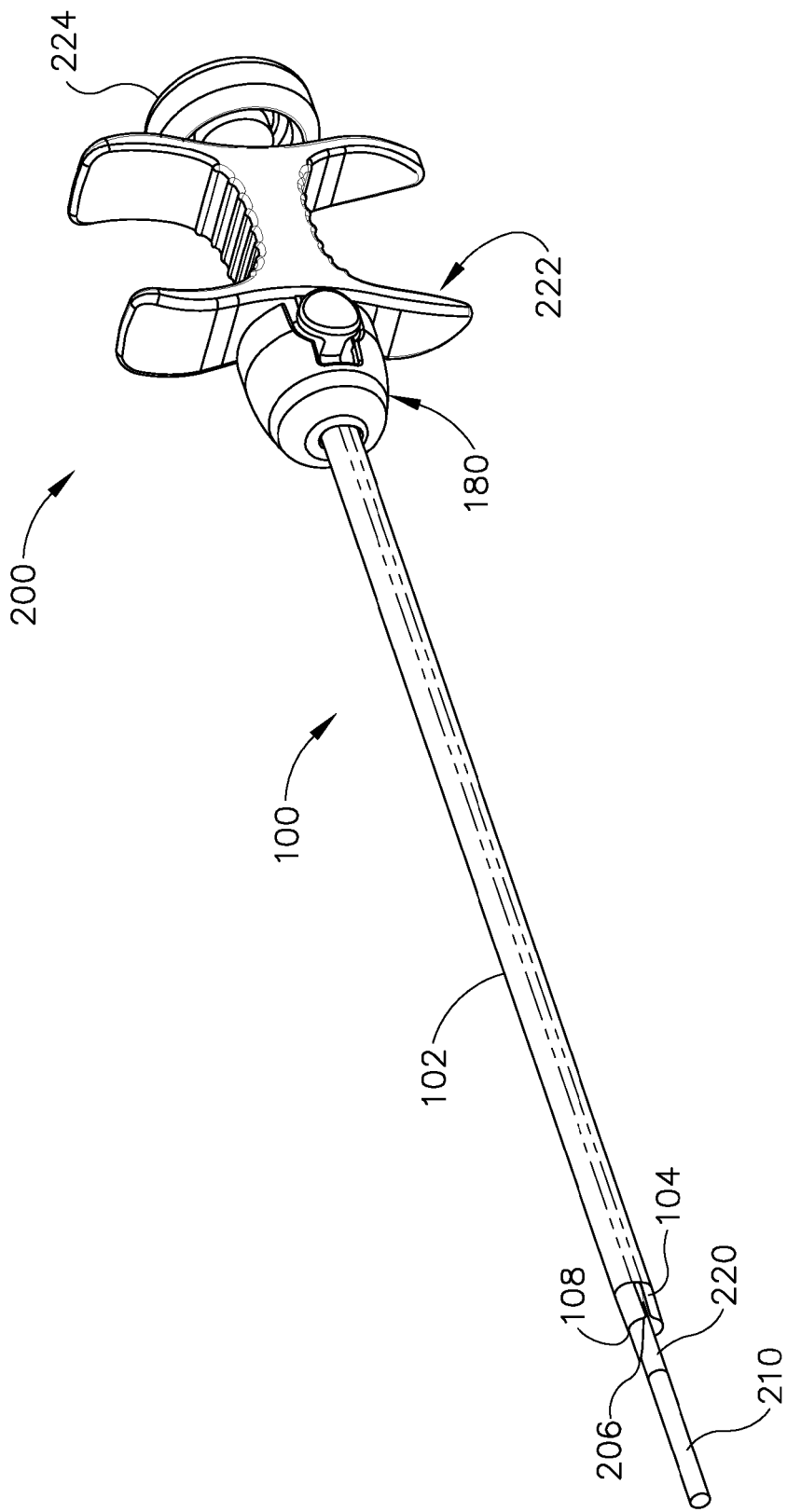
FIG. 5 depicts a perspective view of the marker applier of FIG. 4A inserted in the introducer cannula of FIG. 1A, with the plunger of the marker applier in a distal position to deploy a marker.

As shown in FIG. 5, cannula (202) of marker applier (200) may be inserted through cannula (102) of introducer (100) to deploy marker (210) at a biopsy site after needle (50) of biopsy device (10) has been withdrawn from cannula (102) of introducer (100). As shown, the lengths of cannulas (102, 202) are such that distal end (204) of marker applier (200) protrudes distally from distal end (106) of introducer (100). It should be understood that distal end (204) of marker applier (200) may protrude distally from distal end (106) of introducer (100) to any suitable extent. In the present example, latching feature (180) does not couple with any component of marker applier (200), though in some other versions latching feature (180) may couple with a component of marker applier (200). Still other suitable components, features, configurations, and relationships for introducer (100) and marker applier (200) will be apparent to those of ordinary skill in the art in view of the teachings herein.

Figure 7:
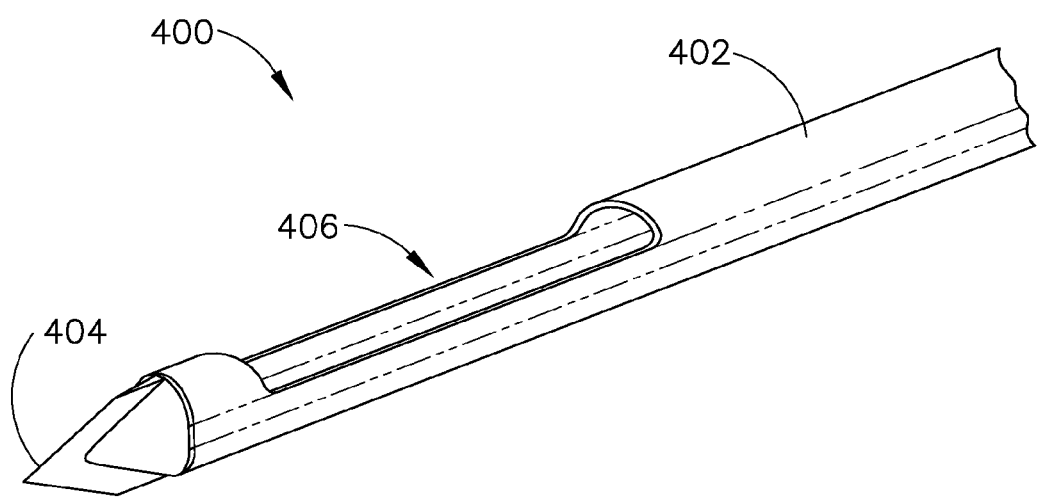
FIG. 7 depicts a perspective view of an exemplary alternative distal end configuration for the introducer cannula of FIG. 1A.

III. Exemplary Introducer Cannula with Closed Distal End and Ramped Proximal Inner Face FIGS. 7-8B show an exemplary alternative needle (300) and introducer (400). It should be understood that needle (300) may be used instead of needle (50) for biopsy device (10). Similarly, it should be understood that introducer (400) may be used instead of introducer (100). Thus, proximal portions of needle (300) and introducer (400) may be configured just like proximal portions of needle (50) and introducer (100) as described above. Furthermore, needle (300) and introducer (400) may be used just like the use of needle (50) and introducer (100) as described above. Of course, needle (300) and/or introducer (400) may have any other suitable alternative configurations; and needle (300) and/or introducer (400) may be used in various other suitable ways.

Figure 6:
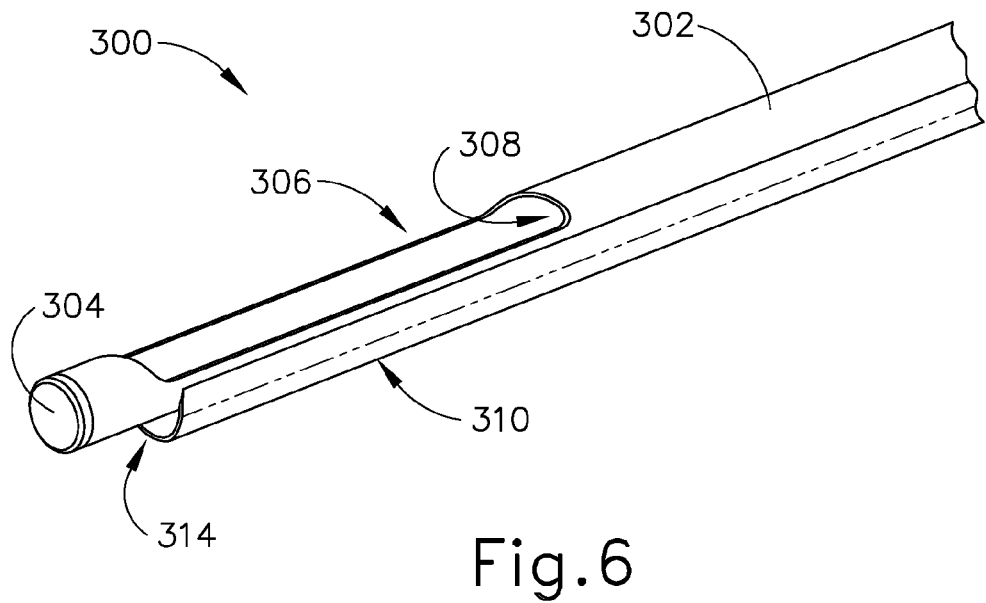
FIG. 6 depicts a perspective view of an exemplary alternative distal end configuration for the needle of the biopsy device of FIG. 1A.

As shown in FIG. 6, needle (300) of the present example includes a cannula (302) having a blunt closed distal end (304) and a lateral aperture (306) located proximal to closed distal end (304). A lower channel region (310) includes an open distal end (314). Open distal end (314) is located at a longitudinal position that is proximal to the longitudinal position of closed distal end (304). As best seen in FIG. 8B, cannula (302) defines a first lumen (308) that is configured to receive a cutter (70). As can also be seen in FIG. 8B, a longitudinal wall (320) and a distal portion of lower channel region (310) define a second lumen (322), which is lateral to and parallel to first lumen (308). While not shown, it should be understood that one or more openings may be formed in wall (320) to provide fluid communication between second lumen (322) and first lumen (308).

As shown in FIGS. 7 and 8A, introducer (400) of this example comprises a cannula (402), a piercing tip (404), and a lateral aperture (406) located proximal to tip (404). Tissue piercing tip (404) of this example is closed and is configured to pierce and penetrate tissue, without requiring a high amount of force, and without requiring an opening to be pre-formed in the tissue prior to insertion of tip (404). Tip (404) may also be configured to provide greater echogenicity than other portions of introducer (400), providing enhanced visibility of tip (404) under ultrasound imaging. By way of example only, tip (404) may be configured in accordance with any of the teachings in U.S. Non-Provisional patent application Ser. No. 12/875,200. Other suitable configurations that may be used for tip (404) will be apparent to those of ordinary skill in the art in view of the teachings herein.

As best seen in FIGS. 8A-8B, introducer (400) further includes a proximally facing wall (410), a ramp (412), and a shelf (414) extending longitudinally from ramp (412) to wall (410). These features (410, 412, 414) are just proximal to tip (404). As can also be seen in FIG. 8B, lateral apertures (306, 406) are substantially aligned when cannula (302) of needle (300) is inserted in cannula (402) of introducer (400). Furthermore, closed distal end (304) abuts proximally facing wall (410) and is positioned above shelf (414). Open distal end (314) of lower channel region (310) is positioned just proximal to ramp (412). In other words, the longitudinal position of distal end (314) relative to the longitudinal position of distal end (304) provides clearance for ramp (412) and shelf (414) when cannula (302) of needle (300) is inserted in cannula (402) of introducer (400) as shown in FIG. 8B. Furthermore, the vertical height of ramp (412) and the vertical height separating distal ends (304, 314) are substantially similar, further facilitating clearance for ramp (412) and shelf (414) when cannula (302) of needle (300) is inserted in cannula (402) of introducer (400).

In an exemplary use, introducer (400) is coupled with needle (300) as shown in FIG. 8B. With cutter (70) at a distal position to effectively close lateral apertures (306, 406), introducer (400) and needle (300) are then inserted together into a patient's tissue. Tip (404) pierces and penetrates the patient's tissue during this insertion. Cutter (70) is then reciprocated to acquire one or more tissue samples, which are deposited into tissue sample holder (40) (e.g., using vacuum assistance, etc.). Once the desired number of tissue samples have been acquired, needle (300) is decoupled from introducer (400), and cannula (302) is withdrawn from cannula (402), leaving cannula (402) disposed in the patient's tissue. A marker applier may then be inserted into cannula (402) to deposit one or more markers at the biopsy site. In addition or in the alternative, one or more medicaments, brachytherapy pellets, and/or other substances may be applied at the biopsy site through cannula (402). In addition or in the alternative, a variety of other kinds of instruments may be inserted through cannula (402) to reach the biopsy site. Introducer (400) may then be pulled from the patient's tissue. Still other suitable ways in which introducer (400) may be used will be apparent to those of ordinary skill in the art in view of the teachings herein.

Figure 11:
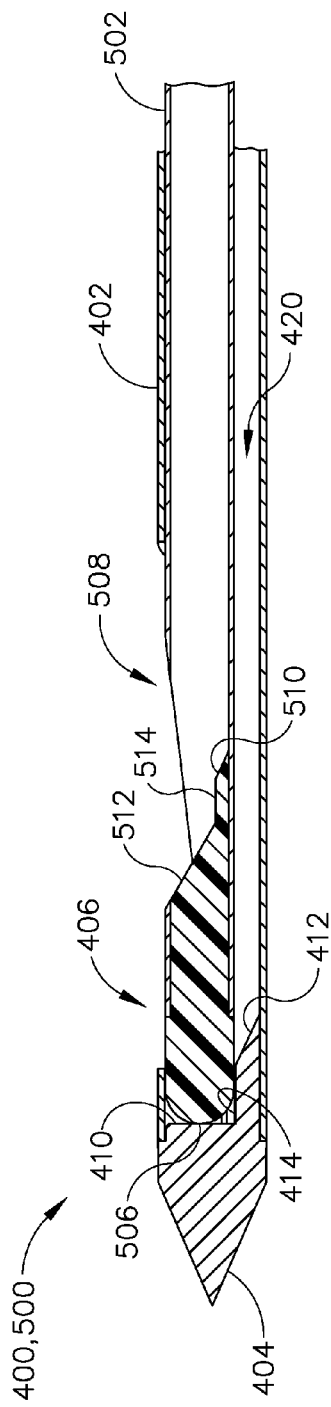
FIG. 11 depicts a partial, side cross-sectional view of the marker applier of FIG. 9 inserted in the introducer cannula of FIG. 7.

As noted above, if needle (300) is withdrawn from introducer (400) with introducer (400) remaining within the patient's tissue, introducer (400) may be used to guide a biopsy site marker applier instrument to the biopsy site for deployment of one or more biopsy site markers. For instance, FIGS. 9-11 show an exemplary marker applier (500) that may be used with introducer (400). Marker applier (500) of this example comprises a cannula (502) having a closed distal end (504) with a round tip (506) and a lateral aperture (508) located proximal to tip (506). Marker applier (500) further includes a first ramp (510), a second ramp (512), and a shelf (514) extending longitudinally from ramp (510) to ramp (512). Ramp (510) is configured to prevent a biopsy site marker (518) from inadvertently falling out through lateral aperture (508) prematurely. Ramp (512) leads to the distal end of lateral aperture (508) and is configured to guide marker (518) out through lateral aperture (508). In particular, a push rod (520) is slidably disposed in cannula (502) and is operable to push marker (210) past ramp (510), along shelf (514), up ramp (512), and out through lateral aperture (508). Marker applier (500) may also include a finger grip and plunger (not shown) that may be manipulated by a single hand of a user to hold marker applier (500) and to advance push rod (520) distally for deployment of marker (518). By way of example only, marker applier (500) comprises a MAMMOMARK™ device from Devicor Medical Products, Inc. of Cincinnati, Ohio in some versions.

As shown in FIG. 11, cannula (502) of marker applier (500) may be inserted through cannula (402) of introducer (400) to deploy marker (518) at a biopsy site after needle (300) has been withdrawn from cannula (402) of introducer (400). As shown, the length of cannulas (402, 502) is such that lateral apertures (406, 508) substantially align when cannula (502)

of marker applier (500) is inserted in cannula (402) of introducer (400). Furthermore, round tip (506) abuts proximally facing wall (410) and is positioned above shelf (414). Round tip (506) is thus trapped between shelf (414) and a distal-most part of the sidewall of cannula (402), distal to lateral aperture (406), such that round tip (506) does not project from lateral aperture (406). As can be seen in FIG. 11, the inner diameter of cannula (402) is substantially larger than the outer diameter of cannula (502), such that a gap (420) is defined between the inner diameter of cannula (402) and the outer diameter of cannula (502). It should therefore be understood that, during initial stages of insertion of cannula (502) of marker applier (500) in cannula (402) of introducer (400), cannula (502) may slide along a lower region of cannula (402) until round tip (506) reaches ramp (412). Ramp (412) may then guide round tip (506) up to shelf (414) and then to wall (410), thus raising distal end (504) of cannula (502). This may assist in properly aligning apertures (406, 508) and may otherwise facilitate proper exit of marker (518) through lateral aperture (406) at the biopsy site. It should also be understood that one or more spacers (not shown) may be positioned along the length of cannula (502) to substantially prevent buckling of cannula (502) within cannula (402), such as in some versions where cannula (502) is formed of a flexible material. Still other suitable components, features, configurations, and relationships for introducer (400) and marker applier (500) will be apparent to those of ordinary skill in the art in view of the teachings herein. It should also be understood that, in some versions, cannula (502) may be fed through cutter (70) when cutter (70) is in a proximal position and when needle (300) is still inserted in introducer (400), such that marker (518) may be deployed through all three apertures (306, 406, 508).

Figure 12:
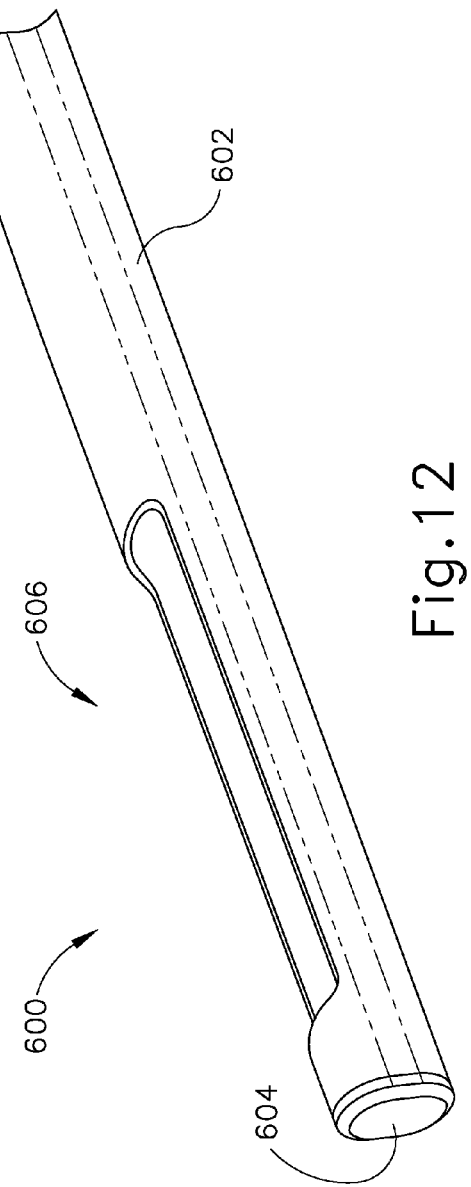
FIG. 12 depicts a perspective view of another exemplary alternative distal end configuration for the needle of the biopsy device of FIG. 1A.

IV. Exemplary Introducer Cannula with Closed Distal End and Flat Proximal Inner Face FIGS. 12-13B show another exemplary alternative needle (600) and introducer (700). It should be understood that needle (600) may be used instead of needle (50) for biopsy device (10). Similarly, it should be understood that introducer (700) may be used instead of introducer (100). Thus, proximal portions of needle (600) and introducer (700) may be configured just like proximal portions of needle (50) and introducer (100) as described above. Furthermore, needle (600) and introducer (700) may be used just like the use of needle (50) and introducer (100) as described above. Of course, needle (600) and/or introducer (700) may have any other suitable alternative configurations; and needle (600) and/or introducer (700) may be used in various other suitable ways.

As shown in FIG. 12, needle (600) of the present example includes a cannula (602) having a blunt closed distal end (604) and a lateral aperture (606) located proximal to closed distal end (604). As best seen in FIG. 13B, cannula (602) defines a first lumen (608) that is configured to receive a cutter (70). As can also be seen in FIG. 13B, a longitudinal wall (620) and a lower region of cannula (602) define a second lumen (622), which is lateral to and parallel to first lumen (608). Wall (620) includes a plurality of openings (624) that provide fluid communication between second lumen (622) and first lumen (608), as well as fluid communication between second lumen (622) and the lumen (not shown) of cutter (70). Openings (624) are arranged such that at least one opening (626) is located at a longitudinal position that is distal to the distal edge of lateral aperture (606). Thus, the lumen of cutter (70) and second lumen (622) may remain in fluid communication even when cutter (70) is advanced to a position where the distal cutting edge of cutter (70) is located at a longitudinal position that is distal to the longitudinal position of the distal edge of lateral aperture (606). Of course, as with any other component described herein, any other suitable configurations may be used.

Figure 13A:
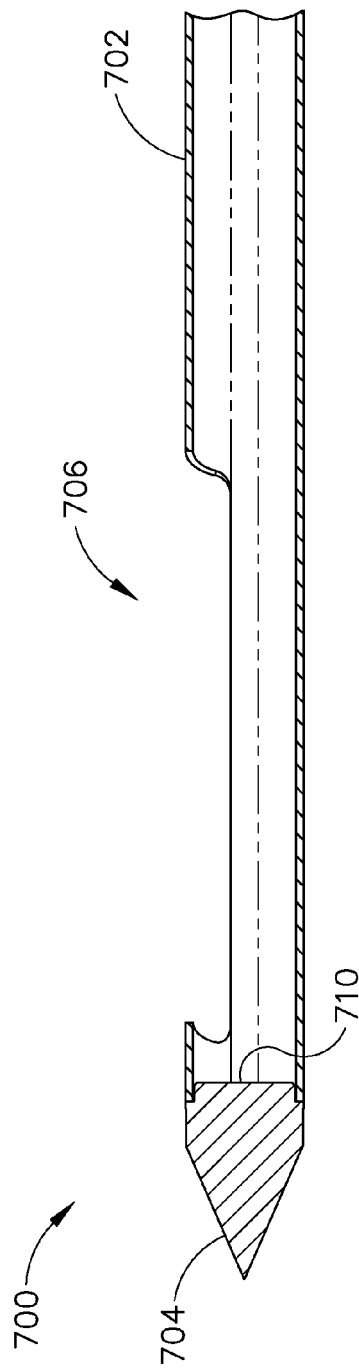
FIG. 13A depicts a partial, side cross-sectional view of another exemplary alternative distal end configuration for the introducer cannula of FIG. 1A.
Figure 13B:
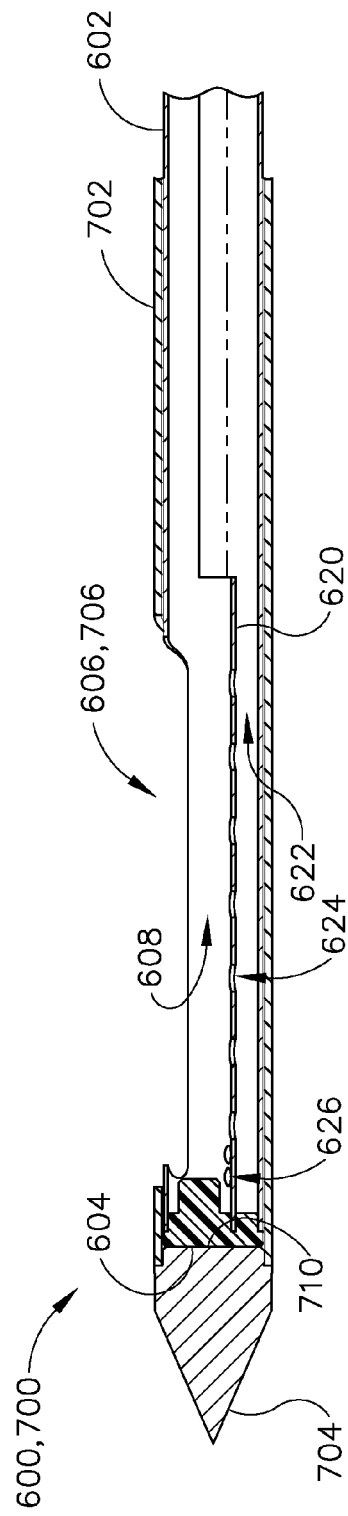
FIG. 13B depicts a partial, side cross-sectional view of the needle of FIG. 12 inserted in the introducer cannula of FIG. 13A.

As shown in FIGS. 13A-13B, introducer (700) of this example comprises a cannula (702), a piercing tip (704), and a lateral aperture (706) located proximal to tip (704). Tissue piercing tip (704) of this example is closed and is configured to pierce and penetrate tissue, without requiring a high amount of force, and without requiring an opening to be pre-formed in the tissue prior to insertion of tip (704). Tip (704) may also be configured to provide greater echogenicity than other portions of introducer (700), providing enhanced visibility of tip (704) under ultrasound imaging. By way of example only, tip (704) may be configured in accordance with any of the teachings in U.S. Non-Provisional patent application Ser. No. 12/875,200. Other suitable configurations that may be used for tip (704) will be apparent to those of ordinary skill in the art in view of the teachings herein. Introducer (700) of this example further includes a proximally facing wall (710), just proximal to tip (704). As can also be seen in FIG. 8B, lateral apertures (606, 706) are substantially aligned when cannula (602) of needle (600) is inserted in cannula (702) of introducer (700). Furthermore, closed distal end (604) abuts proximally facing wall (710).

In an exemplary use, introducer (700) is coupled with needle (600) as shown in FIG. 13B. With cutter (70) at a distal position to effectively close lateral apertures (606, 706), introducer (700) and needle (600) are then inserted together into a patient's tissue. Tip (704) pierces and penetrates the patient's tissue during this insertion. Cutter (70) is then reciprocated to acquire one or more tissue samples, which are deposited into tissue sample holder (40) (e.g., using vacuum assistance, etc.). Once the desired number of tissue samples have been acquired, needle (600) is decoupled from introducer (700), and cannula (602) is withdrawn from cannula (702), leaving cannula (702) disposed in the patient's tissue. A marker applier may then be inserted into cannula (702) to deposit one or more markers at the biopsy site. In addition or in the alternative, one or more medicaments, brachytherapy pellets, and/or other substances may be applied at the biopsy site through cannula (702). In addition or in the alternative, a variety of other kinds of instruments may be inserted through cannula (702) to reach the biopsy site. Introducer (700) may then be pulled from the patient's tissue. Still other suitable ways in which introducer (700) may be used will be apparent to those of ordinary skill in the art in view of the teachings herein.

As noted above, if needle (600) is withdrawn from introducer (700) with introducer (700) remaining within the patient's tissue, introducer (700) may be used to guide a biopsy site marker applier instrument to the biopsy site for deployment of one or more biopsy site markers. For instance, FIGS. 14-15 show an exemplary marker applier (800) that may be used with introducer (700). Marker applier (800) of this example is very similar to marker applier (500) discussed above, except that marker applier (800) includes an additional feature. Marker applier (800) comprises a cannula (802) having a closed distal end (804) with a round tip (806) and a lateral aperture (808) located proximal to tip (806). Marker applier (800) further includes a first ramp (810), a second ramp (812), and a shelf (814) extending longitudinally from ramp (810) to ramp (812). Ramp (810) is configured to prevent a biopsy site marker (not shown) from inadvertently falling out through lateral aperture (808) prematurely. Ramp (812) leads to the distal end of lateral aperture (808) and is configured to guide the marker out through lateral aperture (808). In particular, a push rod (not shown) is slidably disposed in cannula (802) and is operable to push the marker past ramp (810), along shelf (814), up ramp (812), and out through lateral aperture (808). Marker applier (800) may also include a finger grip and plunger (not shown) that may be manipulated by a single hand of a user to hold marker applier (800) and to advance the push rod distally for deployment of the marker. By way of example only, marker applier (800) comprises a modified MAMMOMARK™ device from Devicor Medical Products, Inc. of Cincinnati, Ohio in some versions.

One notable difference between marker applier (800) of this example and both marker applier (500) described above and the MAMMOMARK™ device is that marker applier (800) includes a transversely projecting fin (830) in this example. For instance, fin (830) may be molded as a unitary feature of tip (806) or may comprise a separate component that is secured to tip (806). Fin (830) is substantially rigid and does not move relative to the rest of tip (806) in the present example, though it should be understood that fin (830) may have other properties.

As shown in FIG. 15, cannula (802) of marker applier (800) may be inserted through cannula (702) of introducer (700) to deploy a marker at a biopsy site after needle (600) has been withdrawn from cannula (702) of introducer (700). As shown, the length of cannulas (702, 802) is such that lateral apertures (706, 808) substantially align when cannula (802) of marker applier (800) is inserted in cannula (702) of introducer (700). Furthermore, round tip (806) abuts proximally facing wall (710). As can be seen in FIG. 15, the inner diameter of cannula (702) is substantially larger than the outer diameter of cannula (802), such that a gap (720) is defined between the inner diameter of cannula (702) and the outer diameter of cannula (802). Nevertheless, fin (830) projects transversely from tip (806) to a distance sufficient to keep distal end (804) raised up within cannula (702). This may assist in properly aligning apertures (706, 808) and may otherwise facilitate proper exit of a marker through lateral apertures (706, 808) at the biopsy site. It should also be understood that one or more spacers (not shown) may be positioned along the length of cannula (802) to substantially prevent buckling of cannula (802) within cannula (702), such as in some versions where cannula (802) is formed of a flexible material. Still other suitable components, features, configurations, and relationships for introducer (700) and marker applier (800) will be apparent to those of ordinary skill in the art in view of the teachings herein.

V. Exemplary Marker Applier with Tip Having Resilient Fin

FIGS. 16-19 show yet another exemplary needle (900) and marker applier (1000). In FIGS. 16-19, needle (900) is shown in cross-section while marker applier (1000) is not shown in cross-section. Cutter (970) is shown in cross-section in FIGS. 16 and 18. It should be understood that needle (900) may be used instead of needle (50) for biopsy device (10). Thus, the proximal portion of needle (900) may be configured just like the proximal portion of needle (50) as described above. Needle (900) of this example includes a cannula (902), a piercing tip (904), and a lateral aperture (906) located proximal to tip (904). Tissue piercing tip (904) of this example is closed and is configured to pierce and penetrate tissue, without requiring a high amount of force, and without requiring an opening to be pre-formed in the tissue prior to insertion of tip (904). Tip (904) may also be configured to provide greater echogenicity than other portions of needle (900), providing enhanced visibility of tip (904) under ultrasound imaging. By way of example only, tip (904) may be configured in accordance with any of the teachings in U.S. Non-Provisional patent application Ser. No. 12/875,200. Other suitable configurations that may be used for tip (904) will be apparent to those of ordinary skill in the art in view of the teachings herein.

Needle (900) also defines a lumen (910), in which a cutter (970) is disposed. Lumen (910) distally terminates in a proximally facing wall (912), which is just proximal to tip (904). The difference between the diameter of lumen (910) and the outer diameter of cutter (970) is such that a substantial gap (914) exists between the exterior of cutter (970) and the interior surface of needle (900) that defines lumen (910). As in other examples described herein, cutter (970) reciprocates within needle (900) to sever a tissue sample from tissue protruding through lateral aperture (906). Gap (914) may serve as a second lumen of the type referenced above, such that gap (914) may provide fluid communication to the lumen (972) of cutter (970) (e.g., venting to atmosphere, etc.) during operation. Needle (900) is used without any kind of introducer in this example, though it should be understood that needle (900) may be used with any suitable introducer (e.g., introducer (100), etc.), if desired.

Once cutter (970) has acquired a desired number of tissue samples, marker applier (1000) may be inserted through lumen (972) of cutter (970) and be used to deploy one or more biopsy site markers at the biopsy site. Marker applier (1000) of the present example is substantially similar to marker applier (800) described above. In particular, Marker applier (1000) comprises a cannula (1002) having a closed distal end with a round tip (1006) and a lateral aperture (1008) located proximal to tip (1006). Marker applier (1000) further includes a ramp (1012) that is configured to guide a marker out through lateral aperture (1008). In particular, a push rod (not shown) is slidably disposed in cannula (1002) and is operable to push the marker along ramp (1012) and out through lateral aperture (1008). Marker applier (1000) may further include another ramp and a shelf, such as those described above. Marker applier (1000) may also include a finger grip and plunger (not shown) that may be manipulated by a single hand of a user to hold marker applier (1000) and to advance the push rod distally for deployment of the marker. Other suitable components, features, and configurations will be apparent to those of ordinary skill in the art in view of the teachings herein.

Marker applier (1000) of this example also includes a transversely projecting fin (1030). Fin (1030) is very similar to fin (830) described above, except that in this example fin (1030) is movable relative to the rest of tip (1006). In some versions, fin (1030) is formed entirely or partially of a resilient material that deforms yet is resiliently biased to extend transversely from tip (1006). In addition or in the alternative, fin (1030) may be joined to tip (1006) by a living hinge or other similar feature. In some versions where a living hinge is used to join fin (1030) with tip (1006), the living hinge is resiliently biased to urge fin (1030) to a transverse orientation relative to tip (1006).

Figure 16:
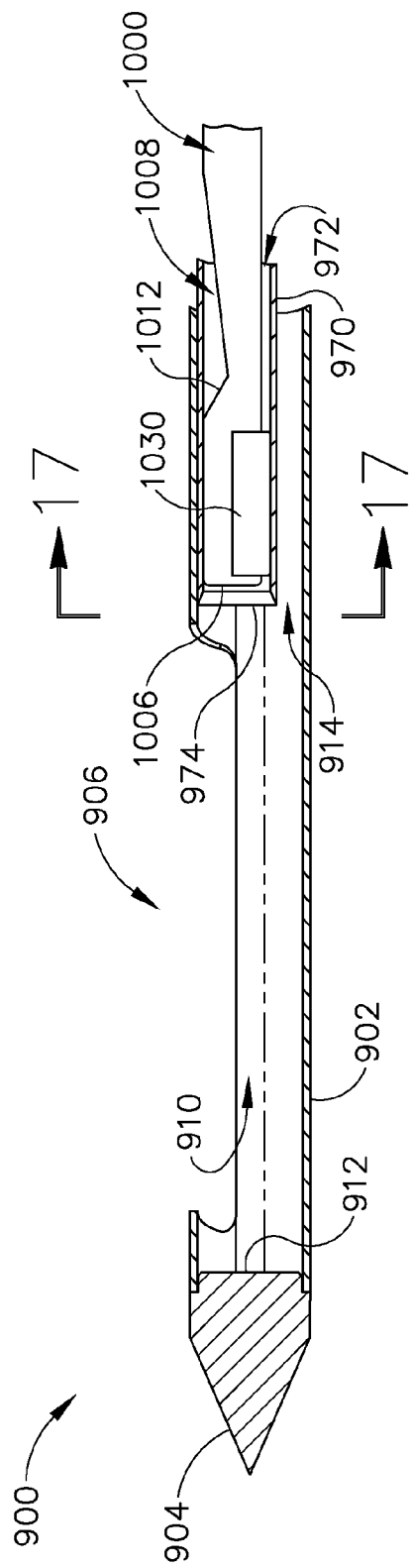
FIG. 16 depicts a partial, side cross-sectional view of another exemplary marker applier disposed in a cutter within another exemplary needle.
Figure 17:
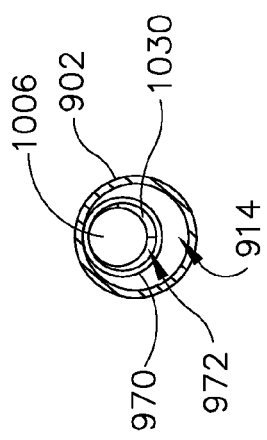
FIG. 17 depicts a cross-sectional view of the marker applier, cutter, and needle of FIG. 16, taken along line 17-17 of FIG. 16.

In an exemplary use, with cutter (970) at a distal position to effectively close lateral aperture (906), needle (900) is inserted into a patient's tissue. Tip (904) pierces and penetrates the patient's tissue during this insertion. Cutter (970) is then reciprocated to acquire one or more tissue samples, which are deposited into tissue sample holder (40) (e.g., using vacuum assistance, etc.). Once the desired number of tissue samples have been acquired, cutter (970) is retracted to a proximal position as shown in FIGS. 16-19, effectively opening lateral aperture (906). Marker applier (1000) is then fed distally through lumen (972) of cutter (970). As tip (1006) and fin (1030) travel through cutter (970), fin (1030) deforms and/or deflects as shown in FIGS. 16-17. This is due to the inner diameter of cutter (970) being smaller than the outer diameter that is otherwise collectively presented by tip (1006) and transversely extending fin (1030). As marker applier (1000) is fed further distally through cutter (970), tip (1006) and fin (1030) eventually clear the distal cutting edge (974) of cutter (970). Upon clearing the restrictive inner diameter of cutter (970), the resilient bias of fin (1030) causes fin (1030) to project transversely as shown in FIGS. 18-19. Marker applier (1000) continues to advance distally until tip (1006) abuts proximal face (912) of needle (900). At this stage, fin (1030) bears against the interior of needle (900) and thereby assists in keeping tip (1006) and lateral aperture (1008) raised up within cannula (902). This further assists in properly aligning apertures (906, 1008), thereby facilitating proper exit of a marker through lateral apertures (906, 1008) at the biopsy site. Still other suitable components, features, configurations, and operabilities for marker applier (1000) will be apparent to those of ordinary skill in the art in view of the teachings herein.

VI. Exemplary Alternative Latching Feature

Figure 20:
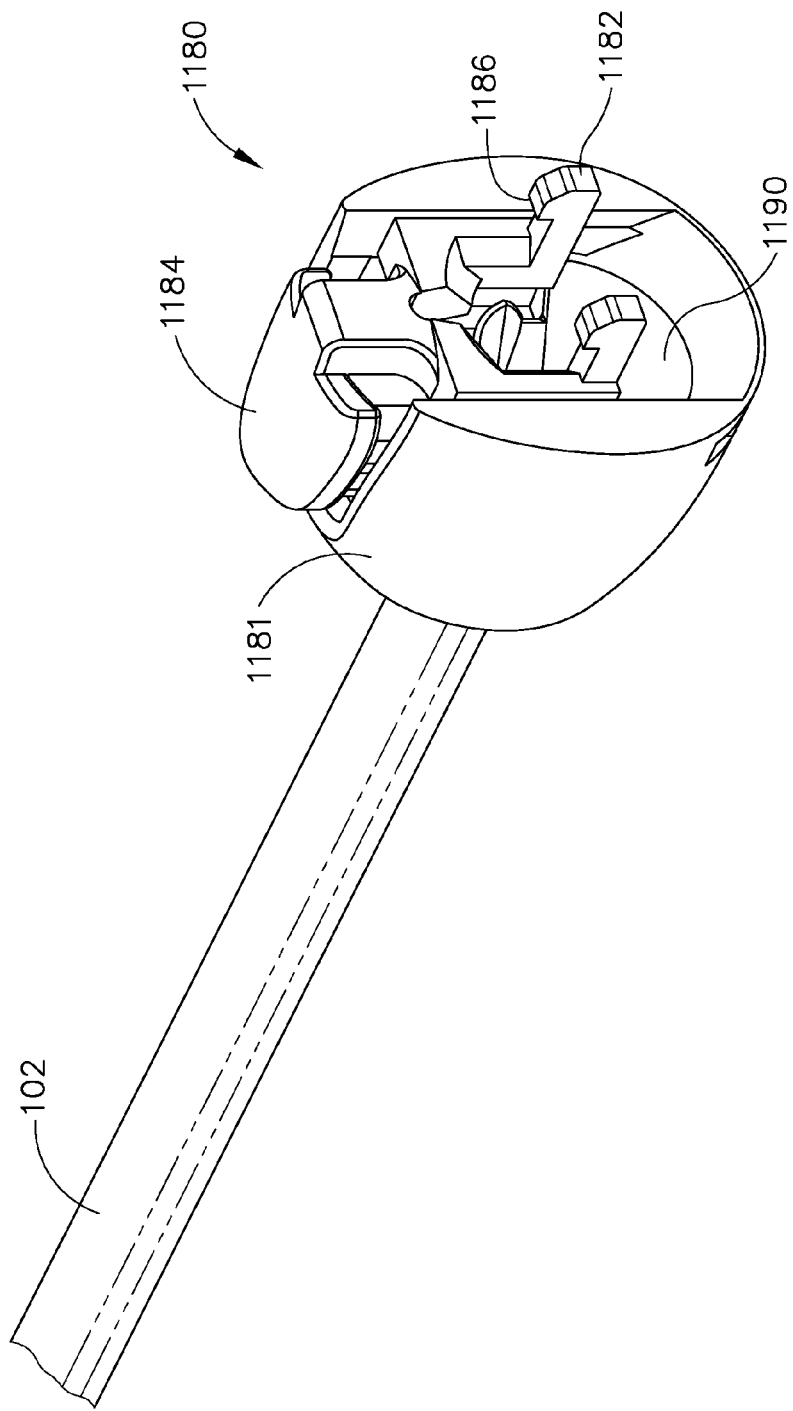
FIG. 20 depicts a perspective view of an exemplary alternative latching feature for an introducer.
Figure 21:
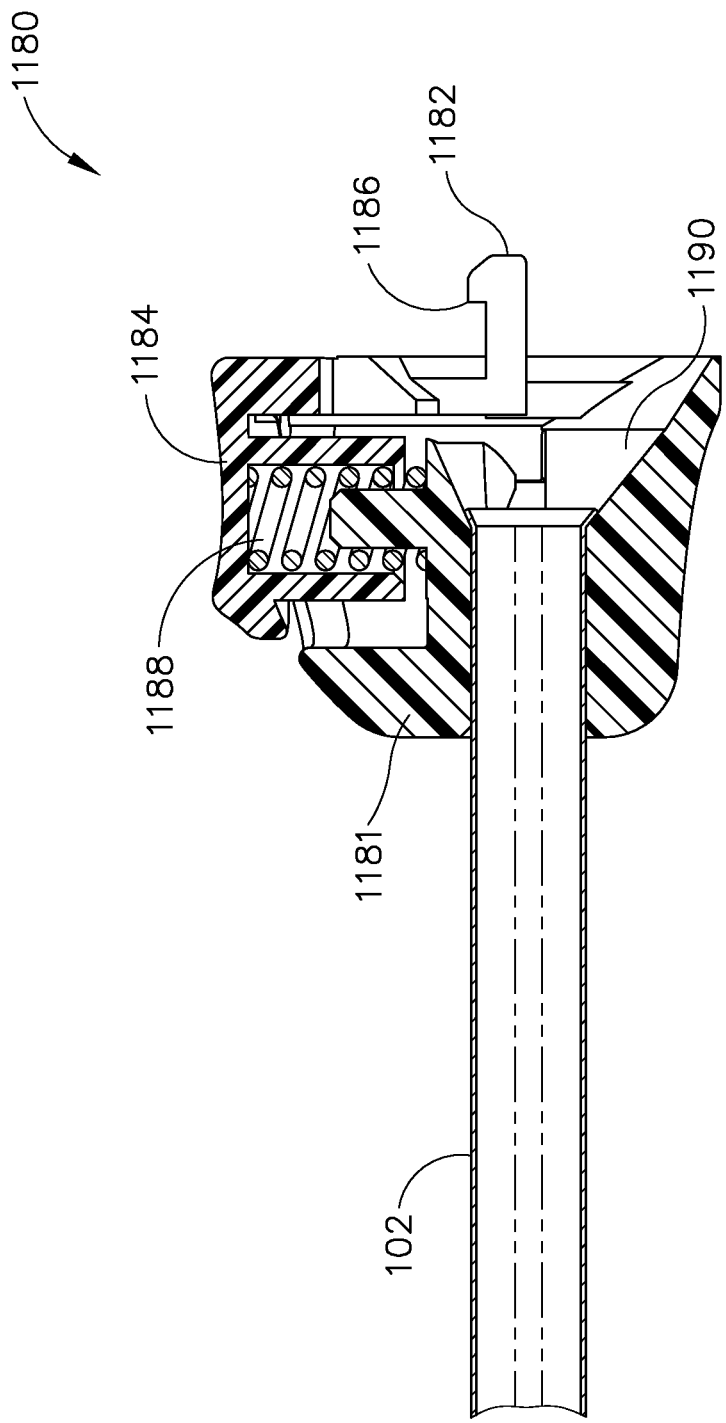
FIG. 21 depicts a side cross-sectional view of the latching feature of FIG. 20.

FIGS. 20-21 show an exemplary alternative latching feature (1180) that may be provided at the proximal end of cannula (102). It should be understood that latching feature (1180) is just one merely illustrative example of an alternative to latching feature (180) described above. It should also be understood that latching feature (1180) may be readily incorporated into any introducer (100, 400, 700) described herein, among various other types of structures into which latching feature (1180) may be incorporated. Latching feature (1180) of this example includes a grip (1181) and a button (1184). A pair of latches (1182) extend from the proximal side of button (1184) and are unitary with button (1184). Latches (1182) include outward projections (1186) that are received in complementary slots of hub member (80) to selectively retain latches (1182) in hub member (80). A coil spring (1188) is positioned between button (1184) and grip (1181), and resiliently biases button (1184) to an upward position. Coil spring (1188) nevertheless allows button (1184) to be pressed toward grip (1181), to correspondingly move latches (1182).

In an exemplary use, a user may insert cannula (52) into cannula (102) via latching feature (1180). A frustoconical ramp (1190) defined by grip (1181) helps guide the distal end of cannula (52) into cannula (102). When latches (1182) reach hub member (80), coil spring (1188) may be compressed to allow projections (1186) to move into engagement with complementary slots of hub member (80). Coil spring (1188) may then expand to hold projections (1186) in engagement with hub member (80) until button (1184) is later pressed to disengage projections (1186) from hub member (80). Still other suitable components, configurations, and operabilities that may be incorporated into a latching feature of an introducer will be apparent to those of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy system, comprising:
   (a) a biopsy device having a needle, wherein the needle includes a closed distal end having a sharp tip, wherein the needle further includes a sidewall defining an outer perimeter, wherein the sidewall comprises two flat sides and two rounded sides, wherein the two flat sides and two rounded sides together define an oval shaped cross-section; and
   (b) an elongated introducer cannula having an open distal end, an open proximal end, and a sidewall, wherein the sidewall includes a pair of opposing flat faces, and a pair of opposing round faces, wherein the flat faces and round faces together define an oval shaped cross-section, wherein the elongated cannula defines a longitudinal axis, wherein the distal end comprises a plurality of leaves, wherein the leaves are separated by a pair of longitudinally extending gaps, wherein the leaves are resiliently biased to deflect inwardly toward the longitudinal axis, wherein the leaves define an opening, wherein the leaves are configured to transition between a stressed position and a relaxed position, wherein, in the relaxed position, the distal edges of the leaves are separated by a gap such that the distal end of the cannula remains open when the leaves are relaxed, wherein an outer edge of each distal leaf extends along a respective axis when the leaves are in the relaxed position, wherein the leaves are configured to transition between the stressed and relaxed positions by engagement with the outer perimeter of the sidewall of the needle, wherein each gap of the pair of longitudinally extending gaps is defined by the leaves to correspond with a respective flat face of the flat faces of the introducer cannula, wherein each flat face of the introducer cannula is associated with a respective flat side of the needle such that the longitudinally extending gaps align with the flat sides of the needle.

2. The biopsy system of claim 1, wherein the needle further includes a lateral aperture formed proximal to the tip, wherein the needle is insertable through the introducer cannula, wherein the needle and the introducer cannula are sized such that the sharp tip and the lateral aperture are positioned distal to the open distal end of the introducer cannula when the needle is inserted in the introducer cannula.

3. The biopsy system of claim 2, wherein the biopsy device and the introducer cannula comprise complementary latching features configured to selectively secure the introducer cannula to the biopsy device.

4. The biopsy system of claim 3, wherein the complementary latching features comprise a slot and a resiliently biased latch member insertable in the slot.

5. The biopsy system of claim 1, wherein the plurality of leaves comprises two leaves.

6. The biopsy system of claim 5, wherein one leaf extends distally further than the other leaf such that the distal end is at an angle relative to the longitudinal axis.

7. The biopsy system of claim 3, wherein the latching features comprise at least one button, wherein the at least one button is resiliently biased to actuate the latching features.

8. The biopsy system of claim 2, further comprising a biopsy site marker applier, wherein the biopsy site marker applier comprises a cannula, wherein the cannula of the marker applier is insertable through the introducer cannula of the introducer, wherein the biopsy site marker applier is operable to deploy a biopsy site marker at a biopsy site.

9. The biopsy system of claim 8, wherein the biopsy device, the biopsy site marker applier, and the introducer cannula comprise complementary latching features configured to selectively secure the introducer cannula to the biopsy device, or the biopsy site marker applier.

10. The biopsy system of claim 1, wherein the proximal end is tapered.

11. A biopsy system, comprising:
(a) an elongated introducer cannula having an open distal end and an open proximal end, wherein the elongated cannula defines a longitudinal axis, wherein the distal end comprises a pair of leaves, wherein the leaves are separated by a pair of longitudinally extending gaps, wherein each gap of the pair of longitudinally extending gaps taper outwardly as each gap extends from a distal end to a proximal end, wherein the leaves define an opening, wherein the leaves are movable between a stressed position and a relaxed position, wherein the leaves are resiliently biased to deflect inwardly toward the longitudinal axis when the leaves are in the relaxed position, wherein a distal edge of each leaf includes a chamfer; and
(b) a biopsy device having a needle, wherein the needle includes a needle cannula and a sharp tip disposed at a distal end of the needle cannula, wherein the needle cannula further includes a lateral aperture formed proximal to the tip, wherein the needle is insertable through the introducer cannula, wherein the needle and the introducer cannula are sized such that the sharp tip and the lateral aperture are positioned distal to the open distal end of the introducer cannula when the needle is inserted in the introducer cannula, wherein the opening defined by the leaves of the introducer cannula has an inner perimeter when the leaves are in the relaxed position, wherein the inner perimeter is sized to permit the sharp tip of the needle to pass through the opening.

12. A biopsy system, comprising
(a) an elongated introducer cannula having an open distal end and an open proximal end, wherein the elongated cannula defines a longitudinal axis, wherein the distal end comprises a pair of leaves, wherein the leaves are separated by a pair of longitudinally extending gaps, wherein each gap of the pair of longitudinally extending gaps includes a rounded proximal end, wherein the leaves are resiliently biased to deflect inwardly toward the longitudinal axis; and
(b) a biopsy device having a needle, wherein the needle includes a closed distal end having a sharp tip, wherein the needle further includes a lateral aperture formed proximal to the tip, wherein the needle further comprises a sidewall defining an outer perimeter, wherein the needle is insertable through the introducer cannula, wherein the needle and the introducer cannula are sized such that the sharp tip and the lateral aperture are positioned distal to the open distal end of the introducer cannula when the needle is inserted in the introducer cannula, wherein the biopsy device and the introducer cannula comprise complementary latching features configured to selectively secure the introducer cannula to the biopsy device, wherein the introducer cannula is configured to be inserted into a patient when the introducer cannula is attached to the biopsy device, wherein the biopsy device is configured to be selectively removed from the introducer cannula after the introducer cannula and biopsy device are inserted into the patient, wherein the opening defined by the leaves of the introducer cannula has an inner perimeter that is smaller relative to the outer perimeter of the needle of the biopsy device such that insertion of the needle of the biopsy device into the introducer cannula causes the leaves to resiliently bear against the sidewall of the needle of the biopsy device while the leaves are positioned away from the sharp tip of the needle.

* * * * *